US011672904B2

(12) United States Patent  
Cabiri et al.

(10) Patent No.: US 11,672,904 B2  
(45) Date of Patent: *Jun. 13, 2023

(54) NEEDLE INSERTION AND RETRACTION MECHANISM

(71) Applicant: West Pharma. Services IL, Ltd., Ra'anana (IL)

(72) Inventors: Oz Cabiri, Hod Hasharon (IL); Ran Hezkiahu, Herzliya (IL); Tal Hammer, Ramat-Gan (IL)

(73) Assignee: West Pharma. Services IL, Ltd., Ra'anana (IL)

(*) Notice: Subject to any disclaimer, the term of this patent is extended or adjusted under 35 U.S.C. 154(b) by 524 days.

This patent is subject to a terminal disclaimer.

(21) Appl. No.: 16/831,989

(22) Filed: Mar. 27, 2020

(65) Prior Publication Data

US 2020/0222625 A1 Jul. 16, 2020

Related U.S. Application Data

(63) Continuation of application No. 16/071,538, filed as application No. PCT/US2016/068367, filed as (Continued)

(51) Int. Cl.
*G10K 9/15* (2006.01)
*A61M 5/142* (2006.01)
(Continued)

(52) U.S. Cl.
CPC ...... *A61M 5/14248* (2013.01); *A61M 5/1413* (2013.01); *A61M 5/1452* (2013.01); (Continued)

(58) Field of Classification Search
USPC ... 340/388.6, 397.2, 393.3, 693.9, 456, 488, 340/521, 612, 679–680
See application file for complete search history.

(56) References Cited

U.S. PATENT DOCUMENTS

| 232,432 A | 9/1880 | Allison |
| 1,125,887 A | 1/1915 | Schimmel |

(Continued)

FOREIGN PATENT DOCUMENTS

| CN | 1505535 A | 6/2004 |
| CN | 1747683 A | 3/2006 |

(Continued)

OTHER PUBLICATIONS

US 8,333,733 B2, 12/2012, Lanigan et al. (withdrawn)

(Continued)

*Primary Examiner* — Daniel Previl
(74) *Attorney, Agent, or Firm* — Blank Rome LLP

(57) ABSTRACT

A system and method are provided for preventing a sharp stick hazard from a needle tip of an automatic injector device. In some embodiments, a skin contact surface of the device is attached to an injection site, for example by an adhesive. Optionally a locking mechanism holds a needle extended into an injection site. A body of the device is optionally movably attached to the skin contact surface. Pulling the body away from the injection site optionally moves the body with respect to the skin contact surface. Movement of the body with respect to the skin contact surface optionally moves interlinked parts of the locking mechanism, releasing the locking mechanism.

20 Claims, 22 Drawing Sheets

Related U.S. Application Data application No. PCT/US2016/056223, filed as application No. PCT/US2016/056247, filed as application No. PCT/US2016/056238 on Oct. 10, 2016, now Pat. No. 10,646,643.

(60) Provisional application No. 62/281,536, filed on Jan. 21, 2016.

(51) Int. Cl.

| | | |
|---|---|---|
| *A61M 5/14* | (2006.01) | |
| *A61M 5/24* | (2006.01) | |
| *A61M 5/145* | (2006.01) | |
| *A61M 5/158* | (2006.01) | |
| *A61M 5/20* | (2006.01) | |
| *A61M 5/32* | (2006.01) | |

(52) U.S. Cl.
CPC .............. *A61M 5/20* (2013.01); *A61M 5/3287* (2013.01); *A61M 2005/14252* (2013.01); *A61M 2005/14256* (2013.01); *A61M 2005/1585* (2013.01); *A61M 2005/206* (2013.01); *A61M 2005/244* (2013.01); *A61M 2005/2492* (2013.01)

(56) References Cited

U.S. PATENT DOCUMENTS

| | | | |
|---|---|---|---|
| 1,321,550 | A | 11/1919 | Platt |
| 1,704,921 | A | 3/1929 | Nicoll |
| 1,795,530 | A | 3/1931 | Cowan et al. |
| 1,795,630 | A | 3/1931 | Wilson |
| 2,453,590 | A | 11/1948 | Poux |
| 2,589,426 | A | 3/1952 | Ogle |
| 2,677,373 | A | 5/1954 | George |
| 2,702,547 | A | 2/1955 | Glass |
| 2,860,635 | A | 11/1958 | Wilburn |
| 3,203,269 | A | 8/1965 | Perrine |
| 3,212,685 | A | 10/1965 | James et al. |
| 3,585,439 | A | 6/1971 | Schneeberger |
| 3,623,474 | A | 11/1971 | Heilman et al. |
| 3,705,582 | A | 12/1972 | Stumpf et al. |
| 3,708,945 | A | 1/1973 | Klettke |
| 3,794,028 | A | 2/1974 | Mueller et al. |
| 3,834,387 | A | 9/1974 | Brown |
| 3,994,295 | A | 11/1976 | Wulff |
| 4,085,747 | A | 4/1978 | Lee |
| 4,189,065 | A | 2/1980 | Herold |
| 4,195,636 | A | 4/1980 | Behnke |
| 4,218,724 | A | 8/1980 | Kaufman |
| 4,254,768 | A | 3/1981 | Ty |
| 4,273,122 | A | 6/1981 | Whitney et al. |
| 4,300,554 | A | 11/1981 | Hessberg et al. |
| 4,324,262 | A | 4/1982 | Hall |
| 4,403,987 | A | 9/1983 | Gottinger |
| 4,425,120 | A | 1/1984 | Sampson et al. |
| 4,435,173 | A | 3/1984 | Siposs et al. |
| 4,465,478 | A | 8/1984 | Sabelman et al. |
| 4,502,488 | A | 3/1985 | Degironimo et al. |
| 4,504,263 | A | 3/1985 | Steuer et al. |
| 4,549,554 | A | 10/1985 | Markham |
| 4,564,054 | A | 1/1986 | Gustavsson |
| 4,565,543 | A | 1/1986 | Bekkering et al. |
| 4,583,974 | A | 4/1986 | Kokernak |
| 4,585,439 | A | 4/1986 | Michel |
| 4,599,082 | A | 7/1986 | Grimard |
| 4,601,702 | A | 7/1986 | Hudson |
| 4,636,201 | A | 1/1987 | Ambrose et al. |
| 4,664,654 | A | 5/1987 | Strauss |
| 4,685,903 | A | 8/1987 | Cable et al. |
| 4,695,274 | A | 9/1987 | Fox |
| 4,698,055 | A | 10/1987 | Sealfon |
| 4,702,738 | A | 10/1987 | Spencer |
| 4,704,105 | A | 11/1987 | Adorjan et al. |
| 4,710,178 | A | 12/1987 | Henri et al. |
| 4,729,208 | A | 3/1988 | Galy et al. |
| 4,735,311 | A | 4/1988 | Lowe et al. |
| 4,737,144 | A | 4/1988 | Choksi |
| 4,772,272 | A | 9/1988 | McFarland |
| 4,810,215 | A | 3/1989 | Kaneko |
| 4,810,249 | A | 3/1989 | Haber et al. |
| 4,813,426 | A | 3/1989 | Haber et al. |
| 4,840,185 | A | 6/1989 | Hernandez |
| 4,850,966 | A | 7/1989 | Grau et al. |
| 4,861,341 | A | 8/1989 | Woodburn |
| 4,863,434 | A | 9/1989 | Bayless |
| 4,867,743 | A | 9/1989 | Vaillancourt |
| 4,874,383 | A | 10/1989 | Mcnaughton |
| 4,882,575 | A | 11/1989 | Kawahara |
| 4,886,499 | A | 12/1989 | Cirelli et al. |
| 4,892,521 | A | 1/1990 | Laico et al. |
| 4,897,083 | A | 1/1990 | Martell |
| 4,900,310 | A | 2/1990 | Ogle, II |
| 4,915,702 | A | 4/1990 | Haber |
| 4,919,569 | A | 4/1990 | Wittenzellner |
| 4,919,596 | A | 4/1990 | Slate et al. |
| 4,923,446 | A | 5/1990 | Page et al. |
| 4,929,241 | A | 5/1990 | Kulli |
| 4,950,241 | A | 8/1990 | Ranford |
| 4,950,246 | A | 8/1990 | Muller |
| 4,957,490 | A | 9/1990 | Byrne et al. |
| 4,964,866 | A | 10/1990 | Szwarc |
| 4,994,045 | A | 2/1991 | Ranford |
| 4,998,924 | A | 3/1991 | Ranford |
| 5,019,051 | A | 5/1991 | Hake |
| 5,051,109 | A | 9/1991 | Simon |
| 5,062,828 | A | 11/1991 | Waltz |
| D322,671 | S | 12/1991 | Szwarc |
| 5,088,988 | A | 2/1992 | Talonn et al. |
| 5,109,850 | A | 5/1992 | Blanco et al. |
| 5,112,317 | A | 5/1992 | Michel |
| 5,114,406 | A | 5/1992 | Gabriel et al. |
| 5,127,910 | A | 7/1992 | Talonn et al. |
| 5,131,816 | A | 7/1992 | Brown et al. |
| 5,147,326 | A | 9/1992 | Talonn et al. |
| 5,156,599 | A | 10/1992 | Ranford et al. |
| 5,190,521 | A | 3/1993 | Hubbard et al. |
| 5,217,437 | A | 6/1993 | Talonn et al. |
| 5,246,670 | A | 9/1993 | Haber et al. |
| 5,254,096 | A | 10/1993 | Rondelet et al. |
| 5,267,977 | A | 12/1993 | Feeney, Jr. |
| 5,269,762 | A | 12/1993 | Armbruster et al. |
| 5,275,582 | A | 1/1994 | Wimmer |
| 5,282,593 | A | 2/1994 | Fast |
| 5,295,966 | A | 3/1994 | Stern et al. |
| 5,298,023 | A | 3/1994 | Haber et al. |
| 5,300,045 | A | 4/1994 | Plassche, Jr. |
| 5,318,522 | A | 6/1994 | D'Antonio |
| 5,338,311 | A | 8/1994 | Mahurkar |
| 5,342,313 | A | 8/1994 | Campbell et al. |
| 5,348,544 | A | 9/1994 | Sweeney et al. |
| 5,366,498 | A | 11/1994 | Brannan et al. |
| 5,376,785 | A | 12/1994 | Chin et al. |
| 5,383,865 | A | 1/1995 | Michel |
| D356,150 | S | 3/1995 | Duggan et al. |
| 5,415,645 | A | 5/1995 | Friend et al. |
| 5,456,360 | A | 10/1995 | Griffin |
| 5,478,315 | A | 12/1995 | Brothers et al. |
| 5,478,316 | A | 12/1995 | Bitdinger et al. |
| 5,482,446 | A | 1/1996 | Williamson et al. |
| 5,496,274 | A | 3/1996 | Graves et al. |
| 5,501,665 | A | 3/1996 | Jhuboo et al. |
| 5,505,709 | A | 4/1996 | Funderburk et al. |
| 5,562,624 | A | 10/1996 | Righi et al. |
| 5,562,686 | A | 10/1996 | Sauer et al. |
| 5,593,390 | A | 1/1997 | Castellano et al. |
| 5,609,580 | A | 3/1997 | Kwiatkowski et al. |
| 5,611,785 | A | 3/1997 | Mito et al. |
| 5,616,132 | A | 4/1997 | Newman |
| 5,624,400 | A | 4/1997 | Firth et al. |
| 5,637,095 | A | 6/1997 | Nason et al. |
| 5,643,218 | A | 7/1997 | Lynn et al. |
| 5,645,530 | A | 7/1997 | Boukhny et al. |

(56) References Cited

U.S. PATENT DOCUMENTS

| | | |
|---|---|---|
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Osterlind et al. |
| 5,690,618 A | 11/1997 | Smith et al. |
| 5,697,908 A | 12/1997 | Imbert et al. |
| 5,697,916 A | 12/1997 | Schraga |
| 5,725,500 A | 3/1998 | Micheler |
| 5,728,075 A | 3/1998 | Levander |
| D393,314 S | 4/1998 | Meisner et al. |
| 5,741,275 A | 4/1998 | Wyssmann |
| 5,766,186 A | 6/1998 | Faraz et al. |
| 5,776,103 A | 7/1998 | Kriesel et al. |
| 5,795,675 A | 8/1998 | Maglica |
| 5,800,420 A | 9/1998 | Gross et al. |
| 5,807,375 A | 9/1998 | Gross et al. |
| 5,810,167 A | 9/1998 | Fujii |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,989,221 A | 11/1999 | Hjertman |
| 5,993,423 A | 11/1999 | Choi |
| 6,004,296 A | 12/1999 | Jansen et al. |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,045,533 A | 4/2000 | Kriesel et al. |
| 6,064,797 A | 5/2000 | Crittendon et al. |
| 6,074,369 A | 6/2000 | Sage et al. |
| 6,162,197 A | 12/2000 | Mohammad |
| 6,186,979 B1 | 2/2001 | Dysarz |
| 6,186,982 B1 | 2/2001 | Gross et al. |
| 6,189,292 B1 | 2/2001 | Odell et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,362,591 B1 | 3/2002 | Moberg |
| 6,377,848 B1 | 4/2002 | Garde et al. |
| 6,391,005 B1 | 5/2002 | Lum et al. |
| 6,423,029 B1 | 7/2002 | Elsberry |
| D461,243 S | 8/2002 | Niedospial |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,554,800 B1 | 4/2003 | Nezhadian et al. |
| 6,555,986 B2 | 4/2003 | Moberg |
| 6,558,351 B1 | 5/2003 | Steil et al. |
| 6,565,541 B2 | 5/2003 | Sharp |
| 6,585,695 B1 | 7/2003 | Adair et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,685,678 B2 | 2/2004 | Evans et al. |
| 6,689,118 B2 | 2/2004 | Alchas et al. |
| 6,699,218 B2 | 3/2004 | Flaherty et al. |
| 6,719,141 B2 | 4/2004 | Heinz et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,783 B2 | 6/2004 | Hung et al. |
| 6,752,787 B1 | 6/2004 | Causey et al. |
| 6,767,336 B1 | 7/2004 | Kaplan |
| 6,768,425 B2 | 7/2004 | Flaherty et al. |
| 6,786,890 B2 | 9/2004 | Preuthun et al. |
| 6,800,071 B1 | 10/2004 | Mcconnell et al. |
| 6,805,687 B2 | 10/2004 | Dextradeur et al. |
| 6,817,990 B2 | 11/2004 | Yap et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,907,679 B2 | 6/2005 | Yarborough et al. |
| 6,908,452 B2 | 6/2005 | Diaz et al. |
| 6,960,192 B1 | 11/2005 | Flaherty et al. |
| 6,979,316 B1 | 12/2005 | Rubin et al. |
| 6,997,727 B1 | 2/2006 | Legrady et al. |
| 7,001,360 B2 | 2/2006 | Veasey et al. |
| 7,004,104 B1 | 2/2006 | Kundus |
| 7,004,929 B2 | 2/2006 | Mcwethy et al. |
| 7,025,226 B2 | 4/2006 | Ramey |
| 7,033,338 B2 | 4/2006 | Vilks et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,063,684 B2 | 6/2006 | Moberg |
| 7,066,909 B1 | 6/2006 | Peter et al. |
| 7,094,221 B2 | 8/2006 | Veasey et al. |
| 7,097,637 B2 | 8/2006 | Triplett et al. |
| 7,112,187 B2 | 9/2006 | Karlsson |
| 7,128,727 B2 | 10/2006 | Flaherty et al. |
| 7,144,384 B2 | 12/2006 | Gorman et al. |
| 7,193,521 B2 | 3/2007 | Moberg et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| RE39,923 E | 11/2007 | Blom |
| 7,291,132 B2 | 11/2007 | Deruntz et al. |
| 7,291,159 B2 | 11/2007 | Schmelzeisen-Redeker et al. |
| 7,303,549 B2 | 12/2007 | Flaherty et al. |
| 7,306,578 B2 | 12/2007 | Gray et al. |
| 7,326,194 B2 | 2/2008 | Zinger et al. |
| 7,344,385 B2 | 3/2008 | Chen |
| 7,364,570 B2 | 4/2008 | Gerondale et al. |
| 7,377,912 B2 | 5/2008 | Graf et al. |
| 7,390,312 B2 | 6/2008 | Barrelle |
| 7,390,314 B2 | 6/2008 | Stutz et al. |
| 7,407,493 B2 | 8/2008 | Cane |
| 7,418,880 B1 | 9/2008 | Smith |
| D578,210 S | 10/2008 | Muta et al. |

(56) References Cited

U.S. PATENT DOCUMENTS

| | | |
|---|---|---|
| 7,442,186 B2 | 10/2008 | Blomquist |
| 7,455,663 B2 | 11/2008 | Bikovsky |
| 7,465,290 B2 | 12/2008 | Reilly |
| 7,468,055 B2 | 12/2008 | Prais et al. |
| 7,488,181 B2 | 2/2009 | Van |
| 7,497,842 B2 | 3/2009 | Diaz et al. |
| 7,500,963 B2 | 3/2009 | Westbye et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | Dibiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| 7,597,682 B2 | 10/2009 | Moberg |
| D604,835 S | 11/2009 | Conley |
| 7,611,491 B2 | 11/2009 | Pickhard |
| 7,621,893 B2 | 11/2009 | Moberg et al. |
| 7,628,770 B2 | 12/2009 | Ethelfeld |
| 7,628,772 B2 | 12/2009 | Mcconnell et al. |
| 7,628,782 B2 | 12/2009 | Mair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,658,734 B2 | 2/2010 | Adair et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| 7,766,867 B2 | 8/2010 | Lynch et al. |
| 7,766,873 B2 | 8/2010 | Moberg et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,892,206 B2 | 2/2011 | Moberg et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,976,514 B2 | 7/2011 | Abry et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 7,998,131 B2 | 8/2011 | Adair et al. |
| 8,002,754 B2 | 8/2011 | Kawamura et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,034,026 B2 | 10/2011 | Grant et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,257,345 B2 | 9/2012 | Adair et al. |
| 8,267,893 B2 | 9/2012 | Moberg et al. |
| 8,267,921 B2 | 9/2012 | Yodfat et al. |
| 8,273,061 B2 | 9/2012 | McConnell et al. |
| 8,287,520 B2 | 10/2012 | Drew et al. |
| 8,292,647 B1 | 10/2012 | Mcgrath et al. |
| 8,303,572 B2 | 11/2012 | Adair et al. |
| 8,308,679 B2 | 11/2012 | Hanson et al. |
| 8,308,695 B2 | 11/2012 | Laiosa |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Lindegger et al. |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |

(56) References Cited

U.S. PATENT DOCUMENTS

| | | |
|---|---|---|
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| 8,500,716 B2 | 8/2013 | Adair et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,517,992 B2 | 8/2013 | Jones |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,617,110 B2 | 12/2013 | Moberg et al. |
| 8,622,966 B2 | 1/2014 | Causey et al. |
| 8,628,510 B2 | 1/2014 | Bazargan et al. |
| 8,632,499 B2 | 1/2014 | Grant et al. |
| 8,647,074 B2 | 2/2014 | Moberg et al. |
| 8,647,296 B2 | 2/2014 | Moberg et al. |
| 8,647,303 B2 | 2/2014 | Cowe |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| D702,834 S | 4/2014 | Norton et al. |
| 8,690,855 B2 | 4/2014 | Alderete et al. |
| 8,708,961 B2 | 4/2014 | Field et al. |
| 8,715,237 B2 | 5/2014 | Moberg et al. |
| 8,721,603 B2 | 5/2014 | Lundquist |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Weinandy |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,845,587 B2 | 9/2014 | Lanigan et al. |
| 8,858,508 B2 | 10/2014 | Lavi et al. |
| 8,864,739 B2 | 10/2014 | Moberg et al. |
| 8,876,770 B2 | 11/2014 | Kraft et al. |
| 8,876,778 B2 | 11/2014 | Carrel |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| 8,979,802 B2 | 3/2015 | Woehr |
| 8,986,250 B2 | 3/2015 | Beebe et al. |
| 9,011,164 B2 | 4/2015 | Filman et al. |
| 9,011,371 B2 | 4/2015 | Moberg et al. |
| 9,011,387 B2 | 4/2015 | Ekman et al. |
| 9,033,925 B2 | 5/2015 | Moberg et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,107,999 B2 | 8/2015 | Moberg et al. |
| 9,138,534 B2 | 9/2015 | Yodfat et al. |
| 9,149,575 B2 | 10/2015 | Cabiri |
| 9,173,996 B2 | 11/2015 | Gray et al. |
| 9,173,997 B2 | 11/2015 | Gross et al. |
| 9,180,248 B2 | 11/2015 | Moberg et al. |
| 9,205,188 B2 | 12/2015 | Lanigan et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| 9,283,327 B2 | 3/2016 | Hourmand et al. |
| 9,308,318 B2 | 4/2016 | Lanigan et al. |
| 9,308,327 B2 | 4/2016 | Marshall et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,339,607 B2 | 5/2016 | Langley et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| 9,364,606 B2 | 6/2016 | Cindrich et al. |
| 9,364,608 B2 | 6/2016 | Moberg et al. |
| 9,381,300 B2 | 7/2016 | Smith et al. |
| 9,393,365 B2 | 7/2016 | Cabiri |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,433,732 B2 | 9/2016 | Moberg et al. |
| 9,433,733 B2 | 9/2016 | Moberg et al. |
| 9,446,188 B2 | 9/2016 | Grant et al. |
| 9,446,196 B2 | 9/2016 | Hourmand et al. |
| 9,452,261 B2 | 9/2016 | Alon |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,622 B2 | 11/2016 | Brereton et al. |
| 9,522,234 B2 | 12/2016 | Cabiri |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,452 B2 | 2/2017 | Adair et al. |
| 9,579,471 B2 | 2/2017 | Carrel et al. |
| 9,610,407 B2 | 4/2017 | Bruggemann et al. |
| 9,656,019 B2 * | 5/2017 | Cabiri ................. A61M 5/1452 |
| 9,656,021 B2 | 5/2017 | Brereton et al. |
| 9,656,025 B2 | 5/2017 | Bostrom et al. |
| 9,707,356 B2 | 7/2017 | Hourmand et al. |
| 9,744,306 B2 | 8/2017 | Cowe |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |
| 9,814,839 B2 | 11/2017 | Eaton |
| 9,849,242 B2 | 12/2017 | Henley et al. |
| 9,862,519 B2 | 1/2018 | Deutschle et al. |
| 9,999,722 B2 | 6/2018 | Yodfat et al. |
| 10,010,681 B2 | 7/2018 | Koch et al. |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,048 B2 | 2/2019 | Gray et al. |
| 10,207,051 B2 | 2/2019 | Cereda et al. |
| 10,227,161 B2 | 3/2019 | Auerbach |
| 10,232,116 B2 | 3/2019 | Ekman et al. |
| 10,258,740 B2 | 4/2019 | Mcloughlin et al. |
| 10,376,641 B2 | 8/2019 | Hirschel et al. |
| 10,376,647 B2 | 8/2019 | Farris et al. |
| 10,434,262 B2 | 10/2019 | Bendek et al. |

(56) References Cited

U.S. PATENT DOCUMENTS

| | | |
|---|---|---|
| 10,500,352 B2 | 12/2019 | Grant et al. |
| 10,561,798 B2 | 2/2020 | Holland et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,646,643 B2 * | 5/2020 | Cabiri .............. A61M 5/14248 |
| 10,722,645 B2 | 7/2020 | Kamen et al. |
| 10,729,847 B2 | 8/2020 | Gray et al. |
| 10,758,679 B2 | 9/2020 | Bar-El et al. |
| 10,842,942 B2 | 11/2020 | Iibuchi et al. |
| 11,027,059 B2 | 6/2021 | Niklaus et al. |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2002/0173748 A1 | 11/2002 | McConnell et al. |
| 2002/0173769 A1 | 11/2002 | Gray et al. |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0125671 A1 | 7/2003 | Aramata et al. |
| 2003/0130618 A1 | 7/2003 | Gray et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0181868 A1 * | 9/2003 | Swenson .......... A61B 5/150717 604/263 |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1 | 1/2004 | Preuthun et al. |
| 2004/0003493 A1 | 1/2004 | Adair et al. |
| 2004/0010207 A1 | 1/2004 | Flaherty et al. |
| 2004/0049160 A1 | 3/2004 | Hsieh et al. |
| 2004/0049161 A1 | 3/2004 | Sheam |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf et al. |
| 2004/0210196 A1 | 10/2004 | Bush et al. |
| 2004/0260233 A1 | 12/2004 | Garibotto et al. |
| 2005/0027255 A1 | 2/2005 | Lavi et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197626 A1 | 9/2005 | Moberg et al. |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsals et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1 | 4/2008 | Spector |
| 2008/0108951 A1 | 5/2008 | Jerde et al. |
| 2008/0119795 A1 * | 5/2008 | Erskine ............ A61M 25/0618 604/263 |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0221523 A1 | 9/2008 | Moberg et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |

(56) References Cited

U.S. PATENT DOCUMENTS

| | | |
|---|---|---|
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De et al. |
| 2009/0143735 A1 | 6/2009 | De et al. |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0010455 A1 | 1/2010 | Elahi et al. |
| 2010/0018334 A1 | 1/2010 | Lessing |
| 2010/0030156 A1 | 2/2010 | Beebe et al. |
| 2010/0030198 A1 | 2/2010 | Beebe |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0241103 A1 | 9/2010 | Kraft et al. |
| 2010/0256486 A1 | 10/2010 | Savage |
| 2010/0264931 A1 | 10/2010 | Lindegger et al. |
| 2010/0268169 A1 | 10/2010 | Llewellyn-Hyde et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0224646 A1 | 9/2011 | Yodfat et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0288526 A1* | 11/2011 | Wei ............... A61M 5/425 604/115 |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Brüggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0118777 A1 | 5/2012 | Kakiuchi et al. |
| 2012/0123387 A1 | 5/2012 | Gonzalez et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Brüggemann et al. |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0267895 A1 | 10/2013 | Hemmingsen |
| 2013/0296799 A1 | 11/2013 | Degtiar et al. |
| 2013/0296824 A1 | 11/2013 | Mo et al. |
| 2013/0304021 A1 | 11/2013 | Cabiri et al. |
| 2013/0310753 A1 | 11/2013 | Cabiri |
| 2013/0310807 A1 | 11/2013 | Adair et al. |
| 2013/0323699 A1 | 12/2013 | Edwards et al. |
| 2013/0331791 A1 | 12/2013 | Gross et al. |

(56) References Cited

U.S. PATENT DOCUMENTS

| | | |
|---|---|---|
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1 | 6/2014 | Cabiri |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207104 A1 | 7/2014 | Vouillamoz et al. |
| 2014/0213975 A1 | 7/2014 | Clemente et al. |
| 2014/0214001 A1 | 7/2014 | Mortazavi |
| 2014/0228768 A1 | 8/2014 | Eggert et al. |
| 2014/0236087 A1 | 8/2014 | Alderete et al. |
| 2014/0243786 A1 | 8/2014 | Gilbert et al. |
| 2014/0261758 A1 | 9/2014 | Wlodarczyk et al. |
| 2014/0343503 A1 | 11/2014 | Holmqvist |
| 2014/0364808 A1 | 12/2014 | Niklaus et al. |
| 2015/0005703 A1 | 1/2015 | Hutchinson et al. |
| 2015/0073344 A1 | 3/2015 | Van Damme et al. |
| 2015/0088071 A1 | 3/2015 | Cabiri |
| 2015/0112278 A1 | 4/2015 | Ray et al. |
| 2015/0119798 A1 | 4/2015 | Gross et al. |
| 2015/0157806 A1 | 6/2015 | Knutsson |
| 2015/0165129 A1* | 6/2015 | Row .................. A61M 5/31501 604/189 |
| 2015/0202375 A1 | 7/2015 | Schabbach et al. |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0144117 A1 | 5/2016 | Chun |
| 2016/0151586 A1 | 6/2016 | Kemp |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0220755 A1 | 8/2016 | Lanigan et al. |
| 2016/0228652 A1 | 8/2016 | Cabiri et al. |
| 2016/0296713 A1 | 10/2016 | Schader et al. |
| 2016/0296716 A1 | 10/2016 | Cabiri et al. |
| 2016/0331900 A1 | 11/2016 | Wei |
| 2016/0339168 A1 | 11/2016 | Hutchinson et al. |
| 2016/0346478 A1 | 12/2016 | Bar-El et al. |
| 2016/0354553 A1 | 12/2016 | Anderson et al. |
| 2017/0007774 A1 | 1/2017 | Brockmeier |
| 2017/0043092 A1 | 2/2017 | Murakami et al. |
| 2017/0058349 A1 | 3/2017 | Levy et al. |
| 2017/0175859 A1 | 6/2017 | Brockmeier |
| 2017/0246399 A1 | 8/2017 | Forlani et al. |
| 2017/0246403 A1 | 8/2017 | Cowe et al. |
| 2018/0028765 A1 | 2/2018 | Waller et al. |
| 2018/0133413 A1 | 5/2018 | Grant et al. |
| 2018/0214637 A1 | 8/2018 | Kemp et al. |
| 2018/0304029 A1 | 10/2018 | Koch et al. |
| 2019/0022306 A1 | 1/2019 | Gibson et al. |
| 2019/0060578 A1 | 2/2019 | Farris et al. |
| 2019/0071217 A1 | 3/2019 | Brown et al. |
| 2019/0099549 A1 | 4/2019 | Lanigan et al. |
| 2019/0175821 A1 | 6/2019 | Kamen et al. |
| 2019/0224415 A1 | 7/2019 | Dugand et al. |
| 2019/0240417 A1 | 8/2019 | Hostettler et al. |
| 2019/0328968 A1 | 10/2019 | Giambattista |
| 2020/0009323 A1 | 1/2020 | Nair et al. |
| 2020/0164151 A1 | 5/2020 | Farris et al. |
| 2020/0215270 A1 | 7/2020 | Ogawa et al. |
| 2020/0297929 A1 | 9/2020 | Zhang |
| 2020/0360602 A1 | 11/2020 | Gray et al. |
| 2021/0138157 A1 | 5/2021 | Bar-El et al. |
| 2021/0220551 A1 | 7/2021 | Dowd et al. |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 101641126 A | 2/2010 |
| CN | 201692438 U | 1/2011 |
| CN | 201941304 U | 8/2011 |
| CN | 102186733 A | 9/2011 |
| CN | 102378638 A | 3/2012 |
| CN | 105102025 A | 11/2015 |
| DE | 0855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0851774 A1 | 7/1998 |
| EP | 0925082 A1 | 6/1999 |
| EP | 1003581 A1 | 5/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2393535 B1 | 3/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| FR | 2770136 A1 | 4/1999 |
| GB | 2436526 A | 10/2007 |
| JP | 62-112566 A | 5/1987 |
| JP | 01-172843 U | 12/1989 |
| JP | 05-062828 A | 3/1993 |
| JP | 07-194701 A | 8/1995 |
| JP | 3035448 U | 3/1997 |
| JP | 09-505758 A | 6/1997 |
| JP | 11-507260 A | 6/1999 |
| JP | 2000-107289 A | 4/2000 |
| JP | 2000-515394 A | 11/2000 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-534061 A | 11/2003 |
| JP | 2004-501721 A | 1/2004 |

(56) References Cited

FOREIGN PATENT DOCUMENTS

| | | |
|---|---|---|
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006-525046 A | 11/2006 |
| JP | 2007-509661 A | 4/2007 |
| JP | 2007-306990 A | 11/2007 |
| JP | 2008-534131 A | 8/2008 |
| JP | 2008-220961 A | 9/2008 |
| JP | 2009-502273 A | 1/2009 |
| JP | 2009-101093 A | 5/2009 |
| JP | 2010-501281 A | 1/2010 |
| JP | 2010-540054 A | 12/2010 |
| JP | 2010-540156 A | 12/2010 |
| JP | 2011-136153 A | 7/2011 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013-530778 A | 8/2013 |
| JP | 2013-531520 A | 8/2013 |
| JP | 2013-531540 A | 8/2013 |
| JP | 2014-030489 A | 2/2014 |
| JP | 2014-515669 A | 7/2014 |
| JP | 2014-518743 A | 8/2014 |
| JP | 2014-521443 A | 8/2014 |
| JP | 2014-525339 A | 9/2014 |
| JP | 2015-514486 A | 5/2015 |
| JP | 2016-525428 A | 8/2016 |
| JP | 2016-530016 A | 9/2016 |
| WO | 90/09202 A1 | 8/1990 |
| WO | 93/07922 A1 | 4/1993 |
| WO | 94/07553 A1 | 4/1994 |
| WO | 94/15660 A1 | 7/1994 |
| WO | 95/13838 A1 | 5/1995 |
| WO | 96/09083 A1 | 3/1996 |
| WO | 96/32975 A1 | 10/1996 |
| WO | 97/00091 A1 | 1/1997 |
| WO | 97/10012 A1 | 3/1997 |
| WO | 97/21457 A1 | 6/1997 |
| WO | 97/33638 A1 | 9/1997 |
| WO | 98/57683 A1 | 12/1998 |
| WO | 98/57686 A1 | 12/1998 |
| WO | 99/29151 A1 | 6/1999 |
| WO | 99/38554 A1 | 8/1999 |
| WO | 99/59665 A1 | 11/1999 |
| WO | 00/25844 A1 | 5/2000 |
| WO | 00/69509 A1 | 11/2000 |
| WO | 01/30415 A2 | 5/2001 |
| WO | 01/30421 A2 | 5/2001 |
| WO | 01/70304 A1 | 9/2001 |
| WO | 01/72357 A2 | 10/2001 |
| WO | 01/87384 A1 | 11/2001 |
| WO | 01/89607 A2 | 11/2001 |
| WO | 01/89613 A1 | 11/2001 |
| WO | 02/02165 A2 | 1/2002 |
| WO | 02/04049 A1 | 1/2002 |
| WO | 02/34315 A1 | 5/2002 |
| WO | 02/38204 A2 | 5/2002 |
| WO | 02/56934 A2 | 7/2002 |
| WO | 02/56943 A2 | 7/2002 |
| WO | 02/72182 A1 | 9/2002 |
| WO | 03/62672 A1 | 7/2003 |
| WO | 03/90833 A1 | 11/2003 |
| WO | 2004/000397 A1 | 12/2003 |
| WO | 2004/032990 A2 | 4/2004 |
| WO | 2004/098684 A2 | 11/2004 |
| WO | 2004/105841 A1 | 12/2004 |
| WO | 2005/018703 A2 | 3/2005 |
| WO | 2005/037350 A2 | 4/2005 |
| WO | 2005/070485 A1 | 8/2005 |
| WO | 2005/072795 A2 | 8/2005 |
| WO | 2006/018617 A1 | 2/2006 |
| WO | 2006/037434 A1 | 4/2006 |
| WO | 2006/052737 A1 | 5/2006 |
| WO | 2006/069380 A1 | 6/2006 |
| WO | 2006/102676 A1 | 9/2006 |
| WO | 2006/104806 A2 | 10/2006 |
| WO | 2006/121921 A2 | 11/2006 |
| WO | 2007/017052 A1 | 2/2007 |
| WO | 2007/051563 A1 | 5/2007 |
| WO | 2007/056504 A1 | 5/2007 |
| WO | 2007/066152 A2 | 6/2007 |
| WO | 2007/073228 A1 | 6/2007 |
| WO | 2007/119178 A2 | 10/2007 |
| WO | 2008/001377 A2 | 1/2008 |
| WO | 2008/014908 A1 | 2/2008 |
| WO | 2008/057976 A2 | 5/2008 |
| WO | 2008/072229 A2 | 6/2008 |
| WO | 2008/076459 A1 | 6/2008 |
| WO | 2008/078318 A2 | 7/2008 |
| WO | 2009/019438 A1 | 2/2009 |
| WO | 2009/022132 A2 | 2/2009 |
| WO | 2009/043000 A1 | 4/2009 |
| WO | 2009/043564 A1 | 4/2009 |
| WO | 2009/044401 A2 | 4/2009 |
| WO | 2009/046989 A2 | 4/2009 |
| WO | 2009/069064 A1 | 6/2009 |
| WO | 2009/125398 A2 | 10/2009 |
| WO | 2009/144085 A2 | 12/2009 |
| WO | 2010/078227 A1 | 7/2010 |
| WO | 2010/078242 A1 | 7/2010 |
| WO | 2010/089313 A1 | 8/2010 |
| WO | 2011/075105 A2 | 6/2011 |
| WO | 2011/090955 A1 | 7/2011 |
| WO | 2011/090956 A2 | 7/2011 |
| WO | WO 2011/101378 A1 | 8/2011 |
| WO | 2011/110872 A1 | 9/2011 |
| WO | 2011/124631 A1 | 10/2011 |
| WO | 2011/129175 A1 | 10/2011 |
| WO | 2011/131778 A1 | 10/2011 |
| WO | 2011/131780 A2 | 10/2011 |
| WO | 2011/131781 A1 | 10/2011 |
| WO | 2011/133823 A1 | 10/2011 |
| WO | 2011/156373 A1 | 12/2011 |
| WO | 2012/003221 A1 | 1/2012 |
| WO | 2012/032411 A2 | 3/2012 |
| WO | 2012/040528 A1 | 3/2012 |
| WO | 2012/145752 A2 | 10/2012 |
| WO | 2012/160157 A1 | 11/2012 |
| WO | 2012/168691 A1 | 12/2012 |
| WO | 2013/036602 A1 | 3/2013 |
| WO | 2013/058697 A1 | 4/2013 |
| WO | 2013/115843 A1 | 8/2013 |
| WO | 2014/132293 A1 | 9/2014 |
| WO | 2014/179117 A1 | 11/2014 |
| WO | 2014/179774 A1 | 11/2014 |
| WO | 2014/194183 A2 | 12/2014 |
| WO | 2015/048791 A1 | 4/2015 |
| WO | 2015/048803 A2 | 4/2015 |
| WO | 2015/078868 A1 | 6/2015 |
| WO | 2015/091758 A1 | 6/2015 |
| WO | 2015/091850 A1 | 6/2015 |
| WO | 2015/114158 A1 | 8/2015 |
| WO | 2015/114428 A1 | 8/2015 |
| WO | 2015/118358 A1 | 8/2015 |
| WO | 2015/163009 A1 | 10/2015 |
| WO | 2016/087626 A1 | 6/2016 |
| WO | 2016/087627 A1 | 6/2016 |
| WO | 2016/141082 A1 | 9/2016 |
| WO | 2017/022639 A1 | 2/2017 |
| WO | 2017/161076 A1 | 9/2017 |
| WO | 2018/222521 A1 | 12/2018 |
| WO | 2019/224782 A1 | 11/2019 |
| WO | 2020/120087 A1 | 6/2020 |
| WO | 2020/193468 A1 | 10/2020 |

OTHER PUBLICATIONS

(56) References Cited

OTHER PUBLICATIONS

Office Action dated Feb. 20, 2015 in U.S. Appl. No. 13/521,181 by Cabiri.
Office Action dated Nov. 6, 2015 in U.S. Appl. No. 14/715,791 by Cabiri.
Office Action dated Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab-le-syringe-system, Download date: Jan. 2009, original posting date: Jun. 2008, 2 pages.
Communication Pursuant to Rules 161 and 162 dated Apr. 6, 2018 in EP Application No. 16784688.0.
Copaxone(Registered), Innovative Drugs, Teva Pharmaceuticals, downloaded from webpage: http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year: 2021).
English translation of an Office Action dated Jan. 30, 2013 in CN Application No. 200880117084.X.
English translation of an Office Action dated Mar. 5, 2014 in CN Application No. 200880117084.X.
European Search Report (Partial) dated Mar. 8, 2017 in EP Application 16193157.1.
Extended European Search Report dated Aug. 7, 2014 in EP Application No. 1417477.4.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report dated Jul. 28, 2020 in European Application No. 20172466.3.
Extended Search Report dated Aug. 7, 2014 in EP Application No. 14171477.4.
Extended Search Report dated Jul. 7, 2017 in EP Application No. 16193157.1.
Int'l Preliminary Report on Patentability dated Nov. 22, 2017 in Int'l Application No. PCT/US2016/068371.
Int'l Search Report and Written Opinion dated Jan. 12, 2011 in Int'l Application No. PCT/US2010/048556; Written Opinion.
Int'l Search Report and Written Opinion dated Jan. 26, 2017 in Int'l Application No. PCT/US2016/056213.
Int'l Search Report and Written Opinion dated Mar. 27, 2017 in Int'l Application No. PCT/US2016/056247.
Int'l Search Report and Written Opinion dated Apr. 21, 2017 in Int'l Application No. PCT/US2016/068367.
Int'l Search Report and Written Opinion dated May 15, 2017 in Int'l Application No. PCT/US2016/068371.
Int'l Search Report and Written Opinion dated Jul. 6, 2017 in Int'l Application No. PCT/US2017/022966.
Int'l Search Report and Written Opinion dated Nov. 28, 2016 in Int'l Application No. PCT/US2016/056218.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Inl'l Application No. PCT/US2016/056227.
Int'l Search Report and Written Opinion dated Dec. 15, 2016 in Inl'l Application No. PCT/US2016/056258.
Int'l Search Repport (Partial), dated Dec. 20, 2016 in Int'l Application No. PCT/US2016/056247.
Int'l Preliminary Report on Patentability dated Jan. 8, 2018 in Int'l Application No. POT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.

(56) References Cited

OTHER PUBLICATIONS

Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Office Action dated Jun. 9, 2017 in EP Application No. 14166591.9.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated Mar. 5, 2014 in CN Application No. 200880117084.X.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.
Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Aug. 17, 2021 in Indian Application No. 201827027625.
Int'l Search Report and Written Opinion dated Jul. 12, 2017 in Int'l Application No. PCT/US2016/056238.
Int'l Search Report and Written Opinion dated Jul. 26, 2013 in Int'l Application No. PCT/US2012/039465.
Int'l Search Report and Written Opinion dated Jul. 31, 2014 in Int'l Application No. PCT/US2014/033598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
Int'l Written Opinion dated Jul. 19, 2012 in Int'l Application No. PCT/US11/21605.
Intel Search Report and Written Opinion dated Nov. 30, 2016 in Int'l Application No. PCT/US2016/056223.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Offce Action dated Sep. 21, 2010 in U.S. Appl. No. 12/244,666 by Gross.
Office Action dated Apr. 22, 2016 in CN Application No. 2014102892041.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178318.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.

(56) References Cited

OTHER PUBLICATIONS

Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6.
Office Action dated Jan. 10, 2017 in U.S. Appl. No. 14/193,692, by Gross.
Office Action dated Jan. 30, 2013 in CN Application No. 200880117084.X.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.

\* cited by examiner

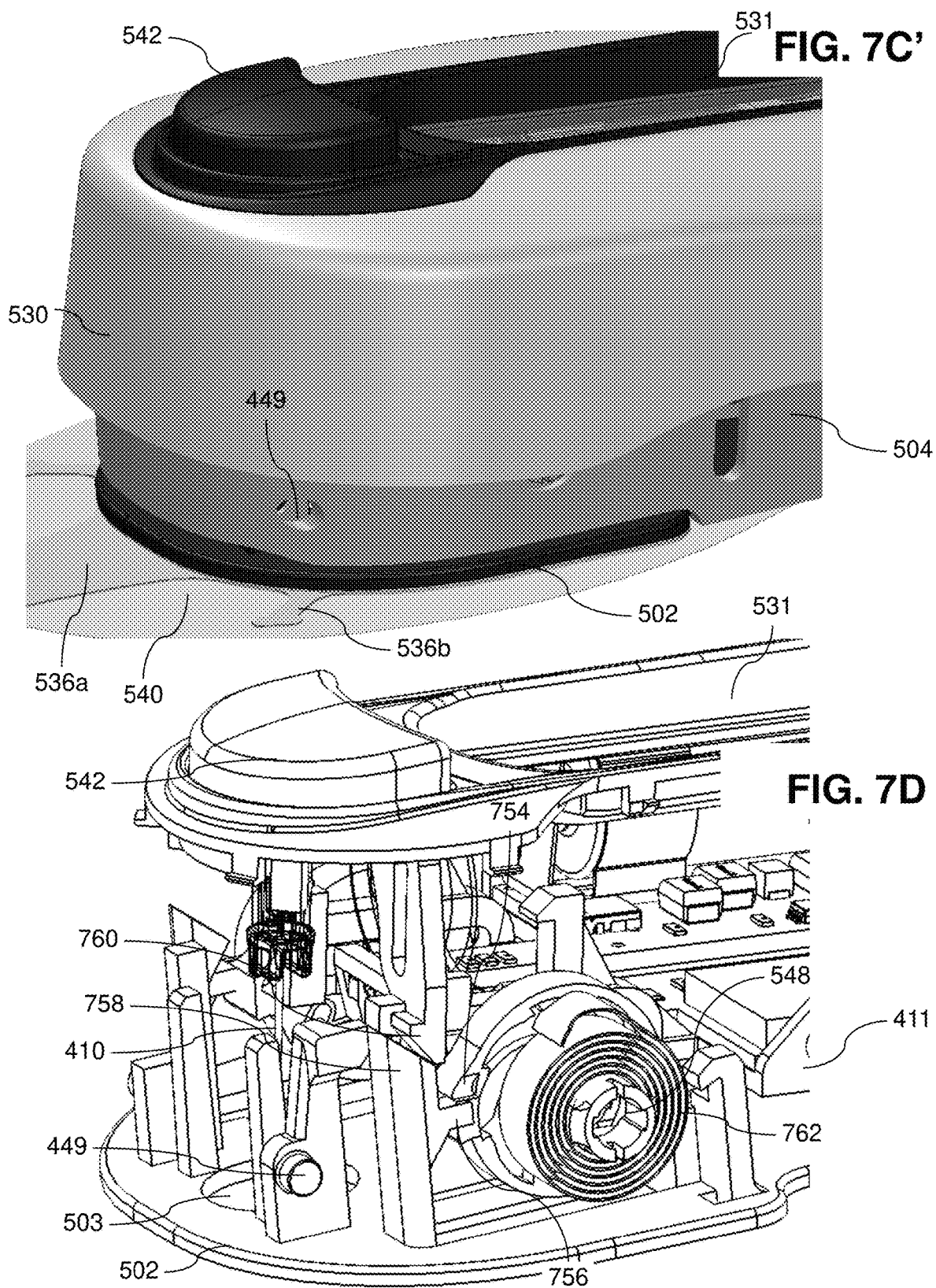

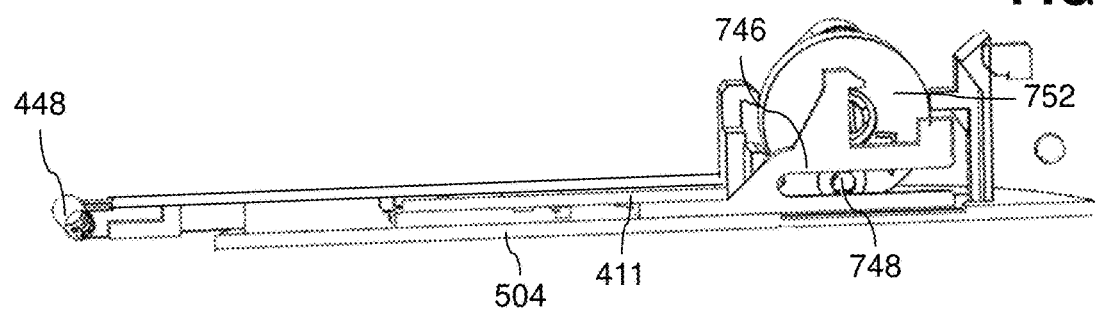
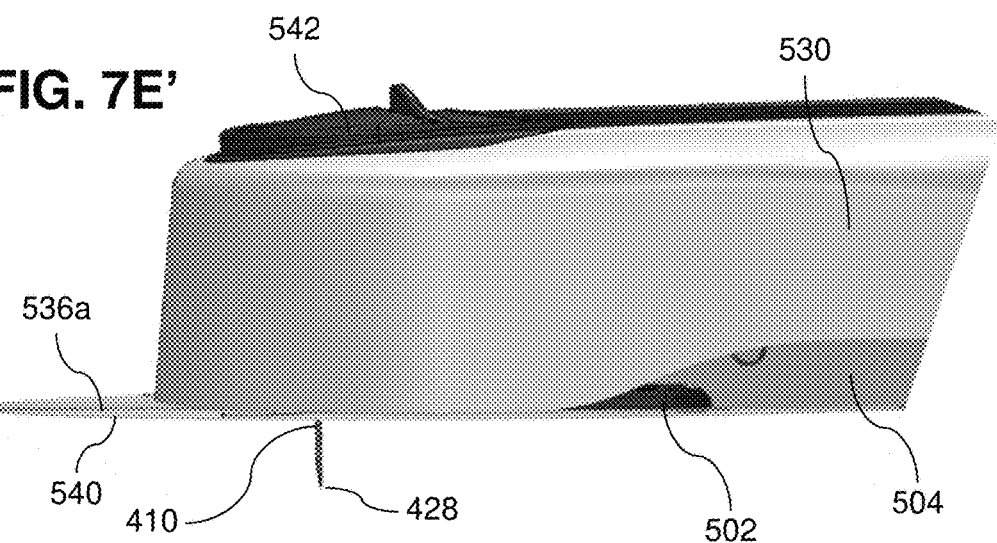
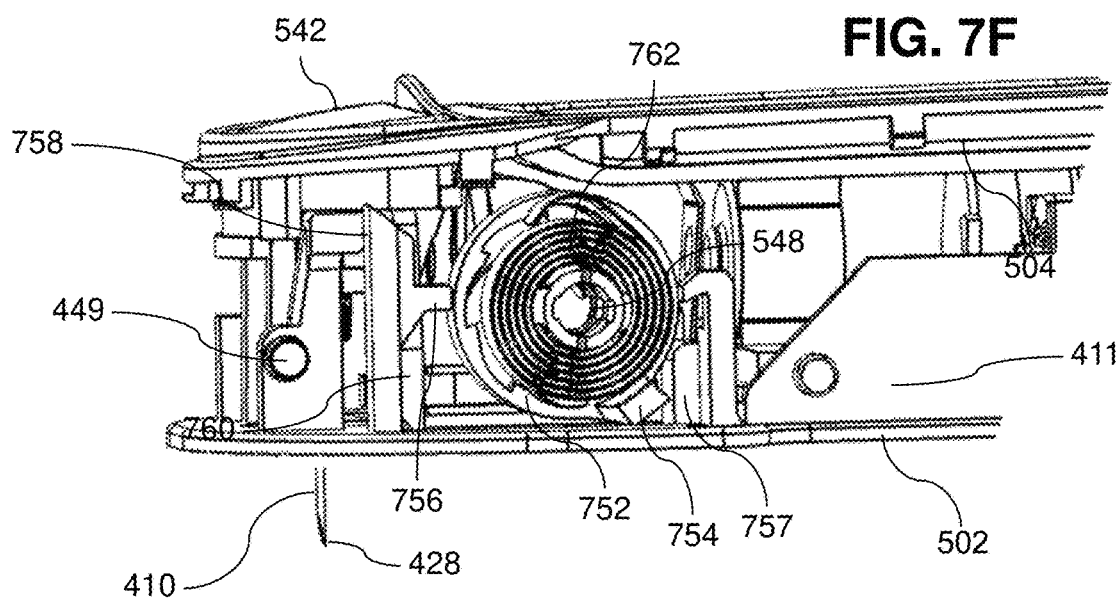

NEEDLE INSERTION AND RETRACTION MECHANISM

RELATED APPLICATION/S

This application claims the benefit of co-pending U.S. patent application Ser. No. 16/071,538, titled "Needle Insertion and Retraction Mechanism", filed Jul. 20, 2018, which is a section 371 of International Application No. PCT/US16/68367, filed Dec. 22, 2016, which was published in the English language on Jul. 27, 2017 under International Publication No. WO 2017/127215 A1, which claims priority to International Application No. PCT/US16/56223, filed Oct. 10, 2016, International Application No. PCT/US16/56238, filed Oct. 10, 2016, International Application No. PCT/US16/56247, filed on Oct. 10, 2016, all of which claim the benefit of U.S. Provisional Application No. 62/281,536, filed Jan. 21, 2016, the disclosures of which are incorporated herein by reference.

FIELD AND BACKGROUND OF THE INVENTION

The present invention, in some embodiments thereof, relates to a system for extending and/or protecting a needle and particularly, but not exclusively, to a system to automatically retract a needle of an auto-injector when the injector is removed from an injection site.

U.S. Pat. No. 9,149,575 apparently discloses, "An apparatus (110) includes an activation mechanism (20) and a safety latch (122). The activation mechanism is operative to deploy a needle (116) to protrude out of a housing (112), the needle (116) having a longitudinal axis. The safety latch (122) is movably mounted on the housing (112) and formed with a needle opening (129) to allow the needle (116) to pass therethrough. The safety latch (122) has a first position wherein the needle (116) is aligned to pass through the needle opening (129) and a second position wherein the safety latch (122) is moved with respect to the housing (112) such that the needle (116) is blocked from movement in a direction parallel to the longitudinal axis thereof by a portion of the safety latch (122) distanced from the needle opening (129)."

U.S. Pat. No. 7,530,964 apparently discloses, "A needle device has a needle retraction mechanism that retracts the needle upon removing the device from the skin surface (either intentionally or unintentionally). Once the needle is retracted, the device is rendered inoperative. The needle can be further made inoperative by bending it when one attempts to reuse the device. In another embodiment, a needle opening formed in the base of the housing can be covered to render the needle inoperative when one attempts to reuse the device. In another embodiment, the needle device instead has a needle shield that automatically covers the needle after use."

U.S. Pat. Nos. 8,915,882, 6,500,150, 6,824,529, and 6,843,782, apparently disclose a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend, which directs the tip of the needle substantially perpendicular to the skin-contacting surface. In use, the tip of the needle is adapted to penetrate the skin of the subject.

For such relatively slow release, an automatic expulsion device has also been suggested. U.S. Pat. No. 5,858,001 discloses a liquid drug delivery device adhered to the skin of a subject by a base member defining a skin-contacting surface having an adhesive coating. A columnar cartridge serves as reservoir for the drug and is incorporated in a housing, which is connected to the base member such that, in use, the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator, which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

If using an injector device then the syringe cartridge may be preloaded and needs to be kept sterile during the process of locating it in the injector. U.S. Patent Publication No. 20140163526 discloses an automated injection device, which may be loaded with a standard type syringe and/or hypodermic needle. Optionally the syringe may be preloaded. The syringe may be loaded into the injector in a sterile state with needle cover in place. The injector includes a fastener, such as an adhesive base. The fastener may assist a user to hold the injector steady on the skin of a patient for an extended period. For example, the injector may be used to give injections of volume ranging between 0.5 and 3.0 ml over a time period ranging between 30 seconds and 10 minutes.

U.S. Pat. No. 8,603,028 relates to a "handheld injection device includes a first housing having a first axis and a second housing having a second axis. In one embodiment, the second housing is configured to support a needle. In one embodiment, the first axis and a second axis form an adjustable angle between about 180 degrees and about 90 degrees."

Additional background art includes U.S. Pat. No. 6,189,292. U.S. Patent Publication No. 20130253434, U.S. Patent Publication No. 2009/093,792, U.S. Pat. No. 7,967,795 U.S. Patent Publication No. 20140194854.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided a system for shielding a needle as an injection device is removed from an injection site: a base including a contact surface having an adhesive for attachment to an injection zone; a tip of a needle movable between an exposed position on a first side of the contact surface to a shielded position on an opposite side of the shielding surface; a lock inhibiting movement of the tip from the exposed position to the shielded position a body movably attached to the base, movable between a first position and a second position distanced from the first position relative to the contact surface; the body linked to the lock to engage the lock to inhibit the movement of the tip from the exposed position to the shielded position when the body is in the first position and the body disengaging the lock to allow movement of the needle tip for the exposed position to the shielded position.

According to some embodiments of the invention, the in the second position, a center of mass of the body is further from the contact surface than in the first position.

According to some embodiments of the invention, the base is positioned between the contact surface and the body of the injector and wherein the body is movable between the first position near the base and the second position distanced from the base.

According to some embodiments of the invention, the system further includes a biasing member biasing the body toward the second position.

According to some embodiments of the invention, the system further includes a retainer that retrains the body in the first position during drug delivery.

According to some embodiments of the invention, the retainer is configured to release the body to the second position in response to pulling the body away from the contact surface of the base.

According to some embodiments of the invention, the retainer includes a second contact surface and a second adhesive such that when the contact surface of the base is attached to an injection zone and the body is in the first position, the second adhesive retains the body in the first position by adhesion.

According to some embodiments of the invention, the second adhesion surface is flush to the adhesion surface of the base when the body is in the first position such that when the body is in the first position and the contact surface of the base is in contact with an injection site on a skin of a subject, the second contact surface also contacts the skin of the subject.

According to some embodiments of the invention, the body is configured to encourage pulling the body away from the injection surface from a position closer to the second contact surface than to the injection zone.

According to some embodiments of the invention, the system further includes an opening in the base and wherein the needle tip is aligned with the opening such that the needle tip passes through the opening when the needle moves from the exposed position to the shielded position.

According to some embodiments of the invention, the needle is aligned with the opening both when the body is in the first position and when the body is in the second position.

According to some embodiments of the invention, the system further includes a sterile needle cap and wherein the opening is large enough for the sterile needle cap to pass therethrough.

According to some embodiments of the invention, the system further includes a stored energy source and wherein the movement of the needle tip is powered by the stored energy source.

According to some embodiments of the invention, the body is shaped and sized for grasping by a human hand, such that grasping the body and pulling it away from the contact surface causes the moving of the body from the first position to the second position.

According to an aspect of some embodiments of the invention, there is provided a method of preventing a stick hazard from a needle tip of a drug delivery device, the device including a body, a skin contact surface, a needle and a lock fixing an orientation of the needle tip with respect to the skin contact surface, the lock including interlinked components attached to the body and the skin contact surface, the method including: Adhering the skin contact surface adhered to injection surface with the needle tip locked protruding from the delivery device into the injection surface; Releasing the lock in response to a reorientation of the interlinked components resulting from a movement of the body relative to the skin contact surface while the skin contact surface remains adhered to the injection surface.

According to some embodiments of the invention, the needle tip is biased to retract through an opening in the contact surface, the method further including, retracting the needle tip in response to the unlocking.

According to some embodiments of the invention, the method further includes pulling the body away from the skin contact surface in order to cause the movement.

According to some embodiments of the invention, the body is adhered to the injection surface to inhibit movement of the body away from the skin contact surface further including Overcoming the adhering of the body to the injection surface by means of the pulling.

According to some embodiments of the invention, the method further includes Biasing the body away from the skin contact surface.

According to some embodiments of the invention, the movement of the body relative to the skin contact surface is in a direction away from the skin contact surface.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-7J are perspective and cut away views of various states of an injector in accordance with an embodiment of the present invention;

DESCRIPTION OF SPECIFIC EMBODIMENTS OF THE INVENTION

Figure 1A:
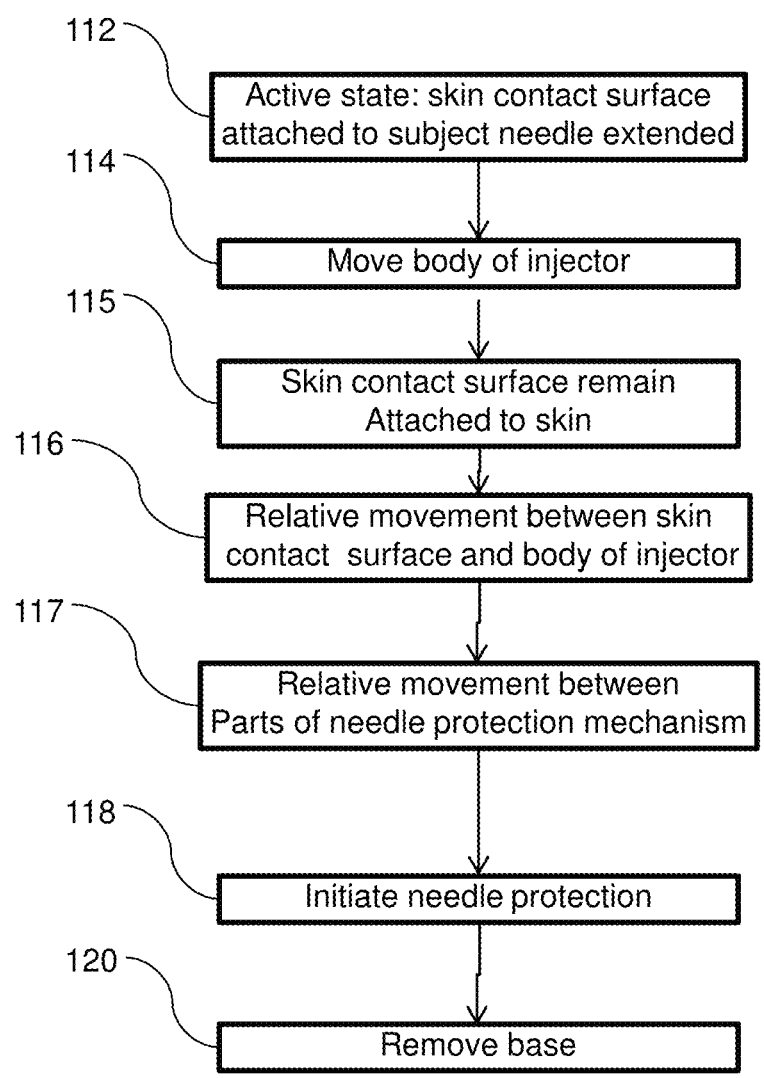
FIG. 1A is a flow chart illustration of a method of protecting a needle in accordance with an embodiment of the present invention.

The present invention, in some embodiments thereof, relates to a system for extending and/or protecting a needle and particularly, but not exclusively, to a system to automatically retract a needle of an auto-injector when the injector is removed from an injection site.

Overview

An aspect of some embodiments of the current invention relates to preventing exposure of a needle of an injector by protecting a needle before a skin contact surface of the injector is removed from an injection surface. For example, a body of the device may be disengaged from the skin contact surface as the device is removed. Disengagement optionally achieves and/or triggers protection of the needle of the injector before the skin contact surface is removed from the injection site.

In some embodiments, an exposed needle is moved to a shielded location when body of the device is moved relative to the injection site and/or a skin contact surface of the device. For example, the body may be moved away from an injection site and or the skin contact surface. For example, the device may include a body (for example including a housing and/or a chassis) that moves with respect to an attachment interface. For example, the body may move from a first location to a second location further away from a contact surface when the shortest distance between the center of mass and the contact surface is larger from the second position than from the first position. For example, the body may move from a first location to a second location further away from an injection site when the shortest distance between the center of mass and point through which the needle tip passes across the contact surface is larger from the second position than from the first position.

An attempt to tamper and/or remove the device from the injection location while a needle tip is exposed optionally causes retraction of the needle into a protected location. For example, the distance of relative movement between the injection site and/or skin contact surface with respect to the body of the device at their closest points may range between 0 to 0.3 mm and/or between 0.3 to 1 mm and/or between 1 mm to 3 mm and/or between 3 mm to 10 mm and/or between 10 mm to 30 mm. Alternatively or additionally, the body may pivot with respect to the injection and/or the skin contact surface to an angle ranging between 0 to 2 degrees and/or between 2 to 6 degrees and/or between 6 to 12 degrees and/or between 12 to 24 degrees and/or between 24 to 45 degrees when the needle retracts. Optionally, the needle may be locked into the protected position. Optionally, movement of the needle to the protected position may be irreversible.

In some embodiments, a sharp hazard may remain covered in many and/or all stages of operation of the device. For example, a needle may be deployed out of a base of a device while the base of the device is attached to an injection site (after the base is connected to the injection site). For example, the needle may be protected while the base remains attached to the injection site (e.g. before the base is removed from the injections site). Optionally, the base may surround the injection site while it is attached thereto. In some embodiments, the base of the device and/or activation may be configured to discourage operation while the base is not connected to the injection site. For example, operation of the device may include placing an adhesive contact surface against an injection site and/or pushing the body of the device toward the contact surface. For example, a user's hesitancy to dirty himself with the adhesive may discourage casual initiation and/or unintentional initiation of the device.

In some embodiments, an injection surface may include a skin surface of a subject. In some embodiments, an injection site may include a site for injecting a pharmaceutical into a subject. Alternatively or additionally, an injection surface may include an artificial surface for demonstrating the device. Alternatively or additionally, an injection surface may include an artificial surface for demonstrating the device.

Alternatively or additionally, an injection surface may include a liquid reservoir in piece of machinery (for example for injecting dye into a printer cartridge).

In some embodiments, a skin sensor and/or contact surface may pivot when an injector is pushed toward an injection site. Optionally, the needle insertion will include pivoting of a cartridge and/or needle assembly. For example, the two pivoting systems may be in opposite directions such that the needle may be oriented at a predetermined angle to the base (for example perpendicular) and/or the angle may be changed when the base is collapsed (for example, due to pushing the device onto the injection site).

Optionally, when the needle is inserted, pivoting of the needle assembly and/or cartridge may partially and/or fully return the needle to the original orientation.

In some embodiments, the base may serve as a proximity and/or skin sensor for stopping and/or protecting the device. For example, when the device is removed from an injection site, the base may be distanced from the body of the injector (for example the housing and/or the chassis and/or the cartridge of the device). Movement of the base with respect to the body of the injector optionally triggers needle protection and/or stops discharge of the drug.

In some embodiments a surface area of a base of the device and/or a skin contact surface thereof and/or an adhesive surface thereof may range between 1 to 5 $cm^2$ and/or 5 to 25 $cm^2$ and/or between 25 to 250 $cm^2$ and/to between 250 to 1000 $cm^2$ and/or between 1000 to 5000 $cm^2$. The base optionally includes between 10 to 70% of the surface area of contact of the device with the skin of a user and/or between 70 to 90% of the surface area of contact of the device with the skin of a user and/or between 90 to 100% of the surface area of contact of the device with the skin of a user.

In some embodiments, a needle opening in base of the device may be large enough to insert and/or remove a sterile needle cover. For example, the width of the opening may range between 1 mm to 2 mm and/or between 2 mm to 4 mm and/or between 4 mm to 10 mm. The cross sectional area of the opening may range for example between 1 to 4 $mm^2$ and/or between 2 to 16 $mm^2$ and/or between 16 to 100 $mm^2$.

In some embodiments, the base of the device is biased towards the body of the device. Alternatively or additionally, the base of the device may be biased away from the body of the device. Optionally, the device may have a retaining mechanism to keep the base from extending away from the body of the device. For example, the retaining mechanism may include an adhesive surface that adheres to the skin of a user and/or keeps the body of the device close to the injection site and/or close to the skin contact surface of the base.

In some embodiments, the force for overcoming the attachment (for example adhesion) of the base to an injection site (for example by pulling the base directly away from the skin surface of a subject) may range of between 0.1 to 1 Newton and/or between 1 to 5 Newtons and/or between 5 to 15 Newtons and/or between 15 to 50 Newtons and/or more. In some embodiments, the force to overcome the retainer that keeps the base close to the body of the device (for example adhesion of the housing to an injection site) for example by pulling the body directly away from the skin surface of a subject may range between 0.1 to 1 Newton and/or between 1 to 5 Newtons and/or between 5 to 15 Newtons. In some embodiments, a force for overcoming the retainer that keeps the base close to the body (for example adhesion of the housing to an injection site) may be for example between 0.1 to 10% and/or between 10% to 25% and/or between 25 to 75% of the force to overcome the attachment of the base to the injection site. In some embodiments, a force may bias a skin contact surface away from a body and/or a chassis of the injector. For example, the biasing force at the location of greatest movement between the contact surface and the body may range between 0.1 to 0.5 Newton and/or between 0.5 to 2 Newtons and/or between 2 to 5 Newtons and/or between 5 to 10 Newtons.

In some embodiments, a base of an injection device may include an adhesive skirt. For example, the adhesive skirt of the base may extend beyond an area where the adhesive is attached to the base between 1 mm to 5 mm and/or between 10 mm to 50 mm. In some embodiments, a base of an injection device may include an adhesive skirt. In some embodiments, a skin contact area of an injector not on the base may include an adhesive skirt. For example, the adhesive skirt of skin contact area not on the base may extend beyond an area where the adhesive is attached to the injector between 0.1 mm to 1 mm and/or between 1 mm to 5 mm. In some embodiments, the adhesive skirt on the base may extend ranging from 10% to 50% and/or from 50% to 250% and/or from 250% to 1000% or more further than the length to which a skirt extends on another skin contact surface of the injector.

In some embodiments a base in movably mounted to a chassis and/or a housing of the injection device. For example, the base may be pivotally mounted thereto.

Optionally a needle assembly and/or the base are movably mounted to the same component. For example, the needle may be mounted on a pivoting arm and/or plate pivoting from one side of a component (for example a chassis) and/or the base may pivot from an opposite side and/or in an opposite direction. For example, when both the needle and the base are collapsed to the body of the device (e.g. the needle extended through an opening in the base and the base collapsed to the chassis) the relative orientation of the needle to the base may be the same as when the basis and needle plate are moved away from the base (for example the needle is retracted and the base is extended away from the chassis).

An aspect of some embodiments of the current invention relates to performing automated initiation of an injection device and/or protection of a sharp needle by user intuitive actions. In some embodiments, an intuitive user interface allows a user with limited preparation and/or knowledge to operate a device based on untrained assumption and/or actions. Optionally an automated user interface performs actions that might arouse avoidance behavior in an unintuitive manner. Optionally, a user interface operates properly even when a user's untrained assumptions lead him to avoid proper activation of the device and/or lead him to act unpredictably and/or perform acts out of order.

In some embodiments, an injector may be activated by simple intuitive acts. For example, initiation may include placing an easily recognizable skin contact surface (for example a flat surface and/or a surface including an adhesive) onto an injection site and/or pushing the body of the injection device towards the injection site and/or depressing an activation button.

In some embodiments, actions that arouse natural avoidance like needle insertion are not a direct result of an intuitive act. Optionally, needle insertion may not occur as a direct mechanical consequence of the user pushes the body towards the skin. For example, needle insertion may be performed automatically by an actuator system. The actuator may optionally be triggered upon proper placement of the injection device onto the skin and/or upon a command (for example pushing a button) and/or through an automated and/or timed control system.

In some embodiments, a needle is automatically protected when a user pulls an injector away from an injection site.

In some embodiments, activation of an injector may require performance of an ordered series of actions. For example, the device may not be activated by a simple act that may be performed inadvertently. For example, the device may be activated by first removing a protective cap and/or then placing a contact surface against the skin and/or then pushing the device into place on the skin and/or then depressing an activation button. Optionally the device will not be activated by performance of only a portion of the actions and/or performance of actions out of order.

In some embodiments, the system will be insensitive to an actions not part of the proper initiation procedure and/or will be insensitive to an act performed out of the prescribed order. For example, an injector may not be affected (for example not activated and/or not disabled) by engaging of an activation switch before proper placement on the injections site. Alternatively or additionally, some improper actions and/or action performed out of order may block activation of the device.

In some embodiments, an injector device may include a user interface.

Optionally the user interface is designed to encourage intuitive and/or proper use of the injector. For example a status indicator and/or a control (for example an activation button) may be located opposite the skin contact surface such that when the contact surface is against the skin, the user sees and/or can reach the user interface.

Alternatively or additionally, the placement of the user interface may encourage the user to hold the injector in a proper way for example for proper placement and operation of the device.

In some embodiments, a needle extension and/or protection system in accordance with the current invention may be included in a patch injector and/or a stabilized pen injector. For example, a patch injector may include a drug reservoir (for example a syringe) having a longitudinal axis parallel (and/or nearly parallel for example between 1 to 10 degrees and/or 10 to 30 degrees) to a skin contact surface or a base of the injector during drug delivery. Optionally, the long axis of the skin contact surface and/or base of a patch injector may be longer than the height of the injector perpendicular to the skin contact surface. In some embodiments, a skin contact surface of a patch injector and/or stabilized pen injector may include a connector for connecting to an injection site.

For example, a connector may include an adhesive. For example, a stabilized pen injector may include a drug reservoir (for example a syringe) having a longitudinal axis perpendicular (and/or at a large angle for example between 90 to 80 degrees and/or 80 to 60 degrees and/or between 60 degrees to 30 degrees) to a skin contact surface or a base. Optionally, the long axis of the skin contact surface and/or base of a stabilized pen injector may be shorter than the height of the injector perpendicular to the skin contact surface.

In some embodiments, needle insertion and/or retraction and/or protection may be automatic. For example, movement of a needle and/or a needle shield (e.g. insertion and/or retraction and/or deployment of a shield and/or withdrawal of the shield) may be powered by an actuator (for example a piston and/or a magnet) and/or a stored energy source (for example a spring and/or a battery). Alternatively or additionally, movement of a needle and/or a needle shield (e.g. insertion and/or retraction and/or deployment of a shield and/or withdrawal of the shield) may be manually powered, for example by pushing an injector and/or a button towards an injection site and/or by pulling the injector away from the site.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Flow Chart of an Exemplary Method of Needle Protection

FIG. 1A is a flow chart illustration of a method of protecting a needle in accordance with an embodiment of the present invention. In some embodiments, a needle is protected automatically when the device is moved away from an injection site.

Optionally the needle is protected before a skin contact surface of the device is removed from the site. For example, the needle may be protected from temporary exposure while the device is being removed. For example, the device may include a base attached to the subject and a body. A needle retraction mechanism may include interlocked parts connected to body and the base. Pulling the body away from the subject may extend the body away from the base and/or disengage the interlocked parts of the retraction mechanism. For example, disengaging the interlocked parts may unlock the needle and/or trigger retraction of the needle.

In some embodiments, an injection device may have an active state 112 wherein a skin contact surface of the device is connected to a needle insertion site, for example on the skin a subject. In the active state 112, a needle is optionally extended into the subject. Optionally, a locking mechanism maintains the needle in the extended position. Alternatively or additionally, the device may include a needle protection mechanism. The locking mechanism and/or needle protection mechanism optionally includes at least one part that moves with the base interlocked to at least one part that moves with the body.

In some embodiments, a user will move 114 the body of the device, for example in order to remove the device from an injection site. Optionally, the user may start removing the device by an intuitive movement. For example, removal may be by pulling the body away from the skin. Optionally, while the body is moved by the user, the skin contact surface remains attached 115 Moving 114 the body optionally causes relative movement 116 between the base and the body.

In some embodiments, the user is encouraged to pull the body from a specific location on the body and/or in a specific direction. For example the housing may have some surfaces that are difficult to pull (for example then are convex and/or face away from the surface and/or low friction) and/or other surfaces that are configured to easily be pulled (for example including indentations for gripping and/or a high friction coating and/or angled toward the skin contact surface). Optionally, there may be markings instructing the user to pull here and/or remove from here etc.

In some embodiments, the body and base of the injector may be free to move relative to each other and/or biased to move relative to each other. Alternatively or additionally, relative movement between the body of the injector and the skin contact surface may be inhibited by a retaining mechanism. For example, the body may be attached to the same surface as the base and/or the body and base may be biased toward one another.

Optionally, the when causing relative movement between the base and the body of the injector, the user may overcome the retaining mechanism. For example, the user may detach the body from the injection site while the base remains attached to the injection site. Alternatively or additionally, at certain times, relative movement may be inhibited (for example during drug delivery) and at other times, relative movement may be facilitated.

For example, at the end of injection the retaining mechanism may be automatically nullified. For example, nullifying the retaining mechanism may facilitate relative movement. Alternatively or additionally, the body of the injector may move on its own respective to the base (e.g. pop up away from the injections site). Optionally, when the retaining mechanism is nullified, the device may remain attached (e.g. by the base) to the injections site.

In some embodiments, relative movement 116 between the base and the body may further cause relative movement between 117 interlocked parts in the needle protection mechanism. The relative movement 117 of parts of the protection mechanism may initiate 118 protection of the needle tip. For example, relative movement 117 may unlock a needle (e.g. allowing it to retract) and/or unlock of a needle shield (e.g. allowing it to extend to cover the needle). For example, relative movement 117 may trigger movement of a needle (e.g. triggering retraction of the needle point) and/or trigger movement of a needle shield (e.g. extending it to cover the needle). For example, initiating 118 and/or initiating protection may include by retracting the needle and/or shielding the needle.

In some embodiments, the device may be removed 120 from the user after the needle is protected. For example, the skin contact surface may be pulled and/or peeled from the injection zone.

Flow Chart of an Exemplary Method of Initiating a Drug Delivery Device

Figure 1B:
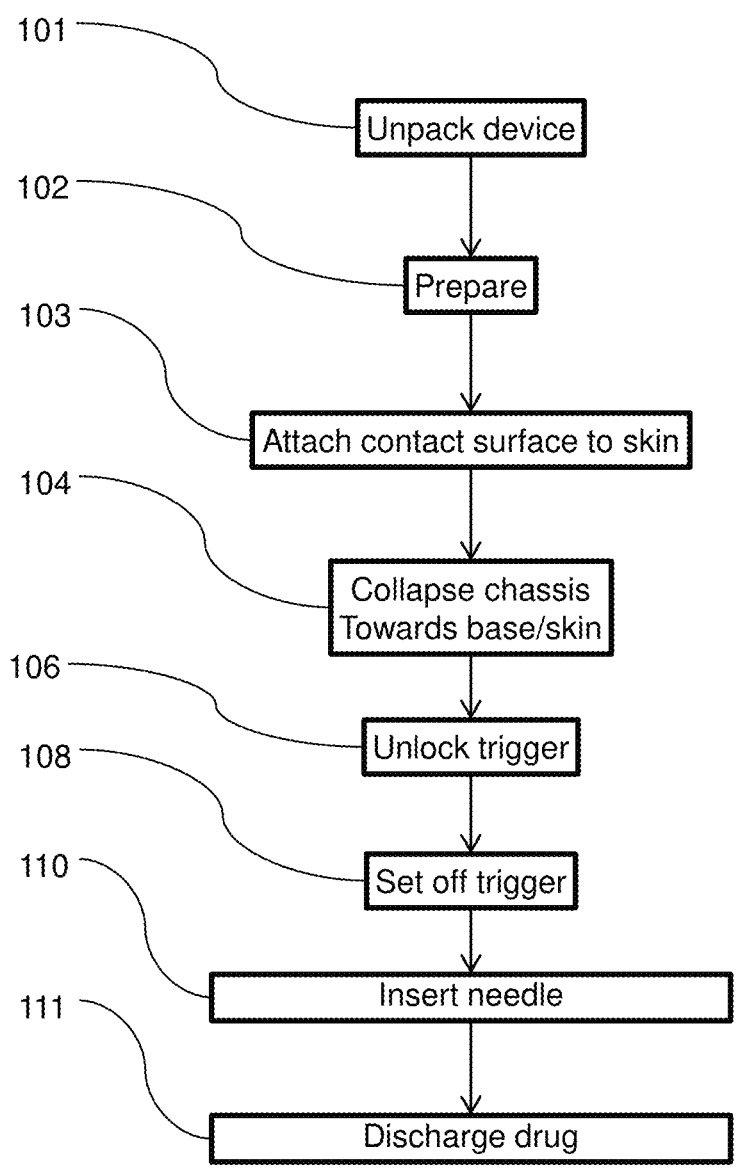
FIG. 1B is a flow chart illustration of a method of extending a needle in accordance with an embodiment of the present invention.

FIG. 1B is a flow chart illustration of initiation of a drug delivery device.

Optionally initiated the device may include extending a needle in accordance with an embodiment of the present invention. Optionally, a user prepares a patch injector for use by simple intuitive steps. Optionally, multiple steps may be performed simultaneously with one act and/or sequentially and/or with multiple acts. Optionally, the a step in preparing the device will cue the user toward the next step, which may include a logical continuation of the preparing. The initiation of the device may be intuitive and/or robust against failure even when misused and/or avoid exposing of a user to hazards under various conditions (proper use, misuse and/or failure).

In some embodiments, the device may be packaged in a way that presents the device in a proper orientation for further preparation of the device. For example, when the packaging is open, the device may be presented to the user in a way that encourages gripping of the device in the proper way for further initiation steps. For example, a griping surface and/or a surface opposite the skin contact surface of the device may be presented to the user upon opening the packaging.

In some embodiments, the packaging may expose a user interface in an early part of unpacking the device. For example, the user interface may be viewable through a window in the packaging before the package is fully opened. Alternatively or additionally, the packaging may be designed such that when the package is opened the user interface faces the user.

Alternatively or additionally, the device may be placed in the packaging such that when the device is unpacked 101 (for example, when it is removed from the packaging) the user interface is exposed to the user. Optionally, the user interface may include familiar operational features. For example, features may include a manually operated feature (for example a pull tab, a pull ring, and/or a button) and/or a display (for example a screen and/or a light and/or a window). The position of the feature may encourage the user to hold the device with the feature operable and/or with the display visible (for example directing his gripping of the device not to cover up a feature and/or orienting the device such that the feature faces the user's limbs and/or eyes).

In some embodiments, a user may prepare 102 a device for use. For example, preparing a device for use may include removing a sterile needle cap and/or removing a protective liner from a skin contact surface. Optionally, multiple components of the device may be interconnected and/or prepared together. For example, a protective needle cap and an adhesive liner may be connected to a single handle, for example a pull ring. Pulling the pull ring optionally removes the cap and the liner together.

Alternatively or additionally, preparing 102 one part may start a process that enables and/or causes preparing 102 of another part.

In some embodiments, a drug delivery device may be attached to a subject. For example, the device may include a skin contact surface that is attached 103 to the skin of the subject. Optionally, attachment 103 is by means of an adhesive. Optionally, the device and/or packaging thereof may be designed to encourage the user to properly attach the device. For example, the skin contact surface may be larger and/or flatter than another surface of the device that does not contact the skin. In some embodiments, the presence of adhesive on the contact surface of the device will serve as an intuitive clue to the user that this surface should be attached to the skin. Optionally, a surface of the device that is not to be attached to the subject may include a feature that intuitively should be exposed, for example an operation feature of the device (e.g. a display and/or a control interface).

In some embodiments, a drug delivery device may include a safety feature to prevent drug delivery before certain steps are performed. For example, in some embodiments, a skin contact surface may serve as a skin sensor. The device may be designed to inhibit extension of a needle and/or discharge of a drug unless the skin contact surface is in contact and/or attached to the subject. For example, an activation button of a drug delivery device may be locked until a skin sensor registers placement of the device on an injection site. For example, the skin sensor may include a skin contact surface. Optionally, when the device has been prepared for use, an activation button may be locked. The button is optionally unlocked 106 by collapsing 104 the skin contact surface into device (for example placing the contact surface onto the injection site and pushing the body of the device towards the skin).

In some embodiments, a drug delivery device may insert a needle through the skin of a subject and/or discharge a drug to the subject. For example, once an activation button is unlocked, pushing the button may cause needle insertion 110 and/or drug delivery 111. In some embodiments, needle insertion is automatic, for example, pressing an activation button may trigger 108 a spring based needle insertion. Alternatively or additionally, force of the user pushing on the activation button may manually extend the needle into the injection site. Alternatively or additionally, the needle may be inserted when the sensor senses contact with the injection site. For example, the user may push the device onto the injection site, collapsing a base of the injector inward, exposing the needle. Alternatively or addition, a sensor may trigger a needle extension mechanism when it senses contact with the injection site.

State Diagram of an Injector

Figure 2A:
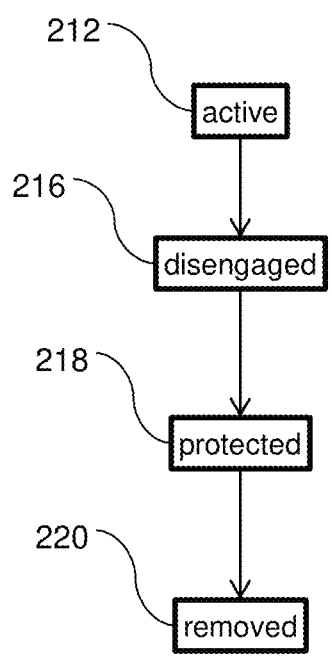
FIGS. 2A and 2B are a state diagram illustration of an injector in accordance with an to embodiment of the present invention.

FIG. 2A is a state diagram illustration of detaching an injector in accordance with an embodiment of the present invention. In some embodiments, an injector may have an ordered set of detachment steps. Optionally some or all of the steps are irreversible. For example, in an active state 212 an attachment surface of the device may be attached to an injection site and/or engaged to body of the device. Disengaging the attachment surface of the device from the body of the device optionally switches the device to a disengaging state 216. Switching the device to disengaging state 216 optionally causes the device to switch to a protected state 218. The device is optionally removed 220 from the injection site after switching to the protected state.

In some embodiments, an injection device may have an active state 212. For example active state 212 may include a working state (e.g. while the device is delivering a drug to a user) and/or a waiting state (e.g. while the device is waiting before delivering a drug and between multiple drug deliveries events and/or after completing delivery).

Optionally, in active state 212 an attachment surface of the device is attached to an injection site and/or supports the device on an injection site. Optionally, in active state 212, a delivery channel, for example a needle and/or a cannula, protrudes into the user at the injection site. For example, the delivery channel may protrude into the user through an opening in the skin contact surface.

In some embodiments, in active state 212, the base of the device may be engaged to the body of the device (for example the body of the device may include a housing of the device and/or a needle driver). For example, the base may be interlocked to the needle driver to lock the needle in an extended position. For example, a part that is attached to the base and/or moves with base may interlock to a part that is attached to the body of the device and/or moves with the body of the device. Alternatively or additionally, in the working state 212 the base may be retained engaged to the body. For example, engagement between the body and the base may expose a needle tip (for example the base may collapse against the body of the device to expose the needle protruding through an opening in the base). Optionally, the base and body may be retained in the engaged state by mutual connection to an external object (for example a surface, for example an area around an injection site). Alternatively or additionally, the base and body may be retained together by a locking mechanism.

In some embodiments, before removing a delivery device from a user, the device may be switched to a disengaged state 216. For example, switching the device a disengaged state may include disengaging the base from the body of the injector.

Optionally the body is disengaged from the base while the base remains attached to the injection site.

In some embodiments, a user action may switch the device from the active to the disengaged state. For example, the user may the pull the body of the device away from the base of the device to disengage the base from the body. Optionally, the user may overcome a retaining mechanism to disengage the base from the body of the device. Alternatively or additionally, under certain conditions, the base may automatically be disengaged from the body of the device. For example, upon completion of drug delivery the body of the device may automatically be disengaged from the base.

In some embodiments, the disengagement is partial. For example, the base may be disengaged from the body by distancing the body from the base while the base still supports the body and/or connects the body to the injections site.

In some embodiments, disengaging a base of the device from a body of the device may trigger and/or facilitate protection of a delivery channel. For example, in the active state a needle may be locked with a needle point in an extended position. The locking mechanism may include engaged parts connected to the body and/or base of the device. Disengaging the base from the body optionally rearranges the engaged parts and/or unlocks the needle allowing the needle to be retracted and/or facilitating retraction of the needle.

In some embodiments, disengaging the base from the body of the device causes the device to switch to a protected state 218. For example, a movement between the base and the body of the device may cause retraction of a needle tip through an opening of the base of the device into a protected position. Alternatively or additionally, relative movement between the base and the body of the device may cause extension of the base to a position shielding the needle. In the protected state 218, the base optionally remains attached to the injection site. Alternatively or additionally, in protected state 218 the base may support the body on the injection site.

In some embodiments, in protected state 218, the device may be removed 220 from the injections site. Optionally, in protected state 218 the needle may be retracted making it easier to separate the device from the injection site. For example, the base may be peeled from the injection site without moving the needle inside the skin of the user and/or without exposing the user to a sharp stick hazard.

Figure 2B:
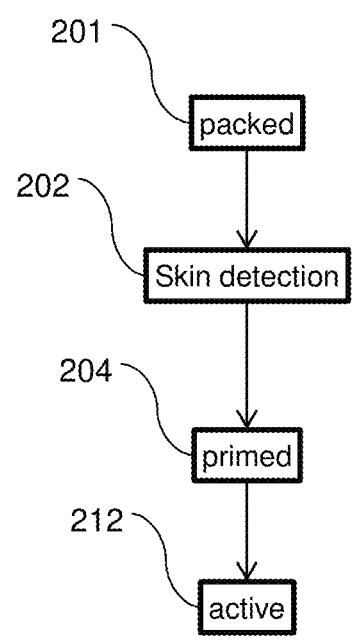

FIG. 2B is a state diagram illustration states of attaching an injector in accordance with an embodiment of the present invention. Optionally, the device is delivered to the user in a packed state 201. Optionally the user unpacks the device and/or prepares the device for attachment to an injection site. For example, a skin sensor may be deployed to put the device in a skin detection state 202. The device may be attached to an injection and/or pushed toward the injection site. Pushing the body of the device towards the injection site optionally stimulates the skin sensor (for example by collapsing a base of the device towards a body of the device). Stimulating the skin sensor optionally switches the device into a primed state 204. Optionally a user action may activate the device from primed state to active state 212. For example, stimulating the skin sensor may enable an activation button and/or pushing the activation button may active the device into active state 212.

Patch Injector

Figure 3:
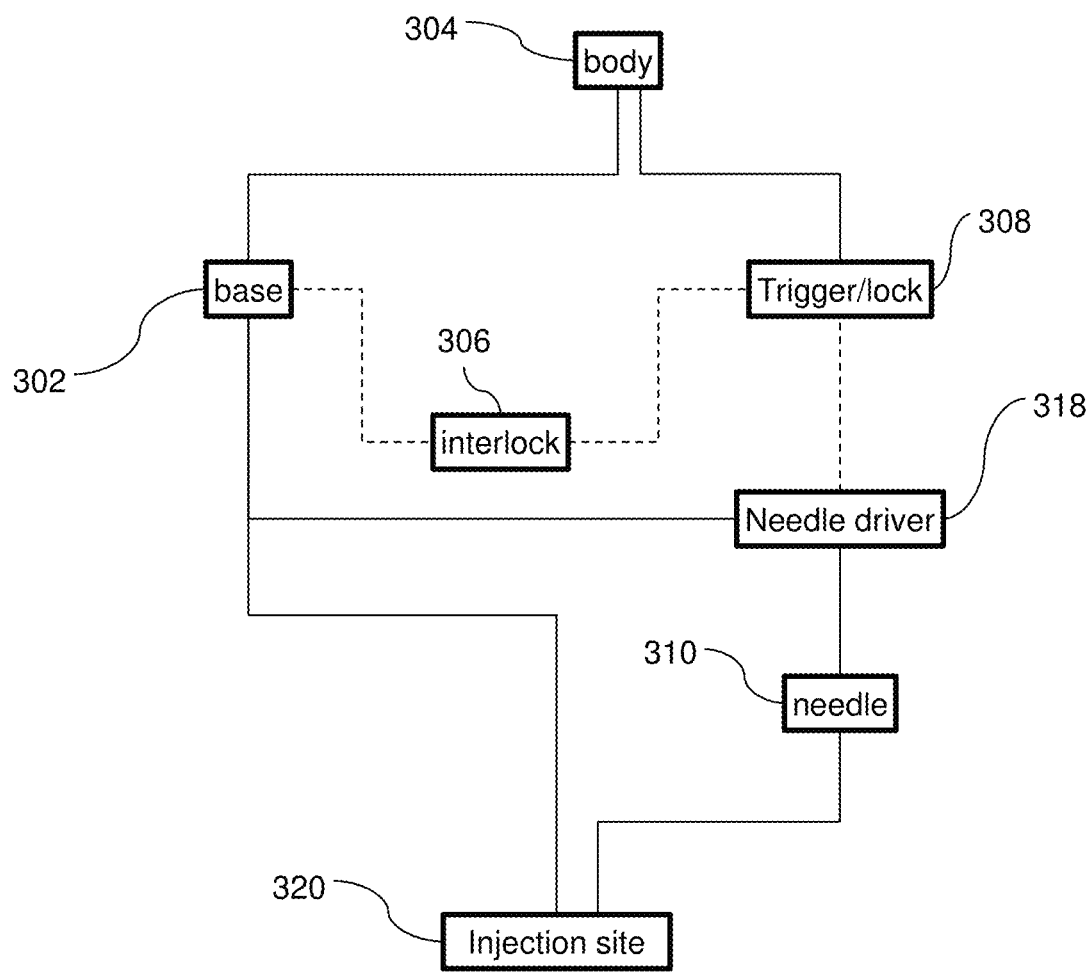
FIG. 3 is a block diagram illustration of a of needle insertion and/or retraction mechanism in accordance with an embodiment of the present invention.

FIG. 3 is a block diagram illustration of an insertion and/or a retraction mechanism in accordance with an embodiment of the present invention. In some embodiments, a base is attached to an injection site. Optionally, the base supports a body of the injector and/or a needle driver. For example, the body may be movably connected to the base. The driver is optionally controlled by a trigger and/or a locking/triggering mechanism. Optionally, the trigger and/or locking mechanism is actuated by the position of the base relative to the body. For example, a mechanical trigger may be mechanically interlocked between the body and base.

In some embodiments, base 302 may include a contact surface configured to attach to an injection site 320. For example, the contact surface may include an adhesive configured to adhere to skin of injection site 320. Optionally, the adhesive on the base is strong enough to support the weight of the entire device. For example, the adhesive may hold the device from falling when the weight is pulling the device away from the injection site and/or the adhesive may prevent sheering movement of the device when the weight is directed parallel to the injection surface. For example, the adhesive on the base may have a surface area between 1 $cm^2$ to 5 $cm^2$ and/or between 5 $cm^2$ to 15 $cm^2$ and/or between 15 $cm^2$ to 80 $cm^2$ or more. Optionally, the adhesive on the base will have a flexible skirt. For example, the skirt may have a length of between 1 mm to 5 mm or between 5 mm to 20 mm or more.

In some embodiments, a body 304 of the device may be connected to the base. For example, the body of the device may include a housing and/or a chassis and/or an energy source and/or a drug reservoir and/or an actuator and/or a pump for discharging the drug through a delivery channel and/or through the injection site into a subject.

Optionally, body 304 and base 302 are connected for relative movement. For example, while base 302 remains attached to injection site 320, body 304 may move relative to the injection site. Optionally, body 304 and base 302 may be connected via a hinge and/or a sliding joint.

In some embodiments, a needle driver 318 may drive insertion and/or retraction of a deliver channel, for example including a needle 310. For example, needle driver 318 may include an elastic element driving movement of needle 310 with respect to the contact surface of base 302. For example, driver 318 may drive extension a sharp tip of needle 310 through an opening in base 302 into the injection site and/or driver 318 may retract the tip of needle 310 through the opening in base 302 back from the injection site. Optionally, driver 318 is mounted to base 302. Alternatively or additionally, driver 318 may be mounted to body 304.

In some embodiments, needle driver 310 is controlled by a locking/triggering mechanism 308. For example, mechanism 308 may trigger retraction and/or extension of needle 310. Optionally mechanism 308 may respond to changes in the relative positions of body 304 and base 302 to trigger retraction and/or extension. For example, when needle 310 is extended, mechanism 308 may retract needle 310 in response to a movement of body 304 away from base 302. For example, when needle 310 is locked in an extended position, mechanism 308 may unlock needle 310 in response to a movement of body 304 away from base 302. In some embodiments, a mechanical linkage may interconnect 306 mechanism 308, base 302 and/or body 304. For example, relative movements of the components may cause physical locking/unlocking and/or trigger insertion/retraction. Alternatively or additionally, mechanism 308 may include an electronic sensor, an electrical switch and/or a logic processor and/or an optical sensor sensitive to relative movements of base 302 and body 304.

In some embodiments, the system may be biased towards retraction and/or extension of needle 310. For example, base 302 may be biased toward body 304 and/or away from the body. Optionally a retaining mechanism may hold body 304 and/or base 302 in a fixed configuration. Optionally a user action will overcome biasing and/or a retention mechanism to extend and/or retract and/or lock and/or unlock needle 310.

For example, in some embodiments, base 302 may be biased away from body 304. Optionally, in an active state, base 302 and body 304 are both attached to an injection site. When a user pulls body 304 away from the injection site, base 302 stays on the site and/or is distanced from base 302. Optionally, distancing base 302 from body 304 triggers needle retraction.

In some embodiments, a discharge mechanism and/or a user interface and/or a logical controller are sensitive to the relative positions of base 302 and body 304. For example, an activation button for discharge may be blocked when base 302 is distanced from body 304. Alternatively or additionally, a logic unit may register and/or communicate an error condition when base 302 moves with respect to body 304 in a way that is not according to the specified order of operation of the device. Optionally the error may lead to locking and/or stopping and/or disabling of certain systems of the device. For example, premature distancing of base 302 from body 304 during drug discharge may cause an error condition and/or cause a stopping of drug delivery. For example, the base may move with respect to the body between 0.1 mm to 1.0 mm and/or between 1 mm to 2 mm and/or between 2 mm to 4 mm and/or between 4 mm to 10 mm and/or between 10 mm to 30 mm. For example, the distance moved may be measured where the maximum relative movement occurs.

Figure 4A:
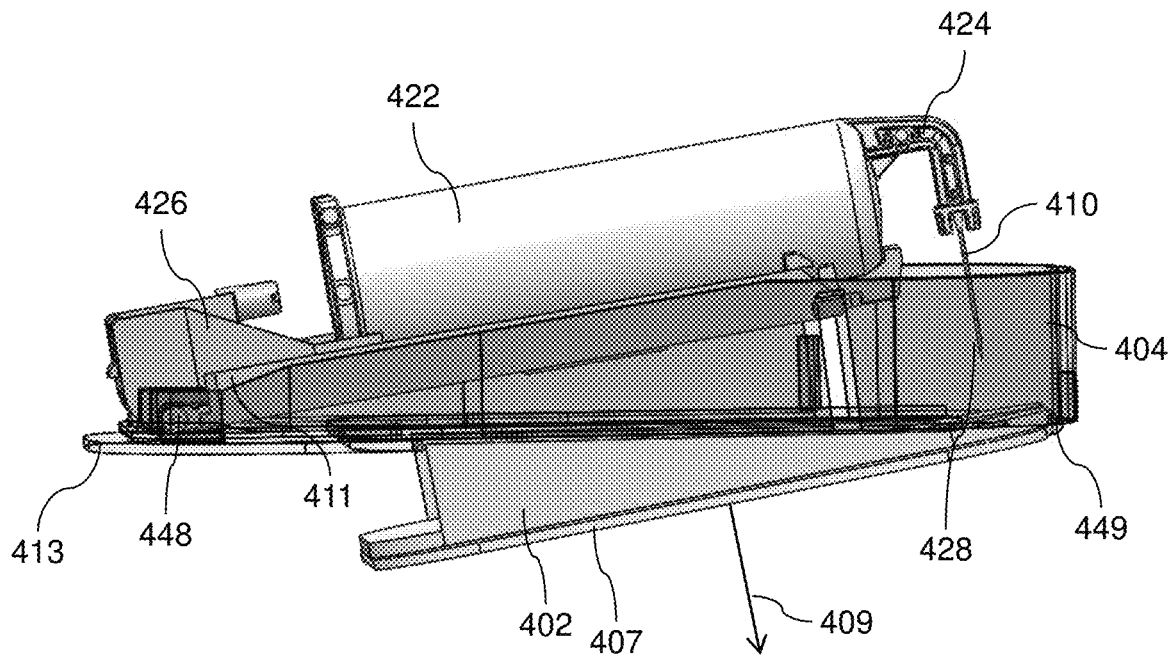
FIGS. 4A-4D are side view illustrations of a four states of an injector in accordance with an embodiment of the present invention.
Figure 4B:
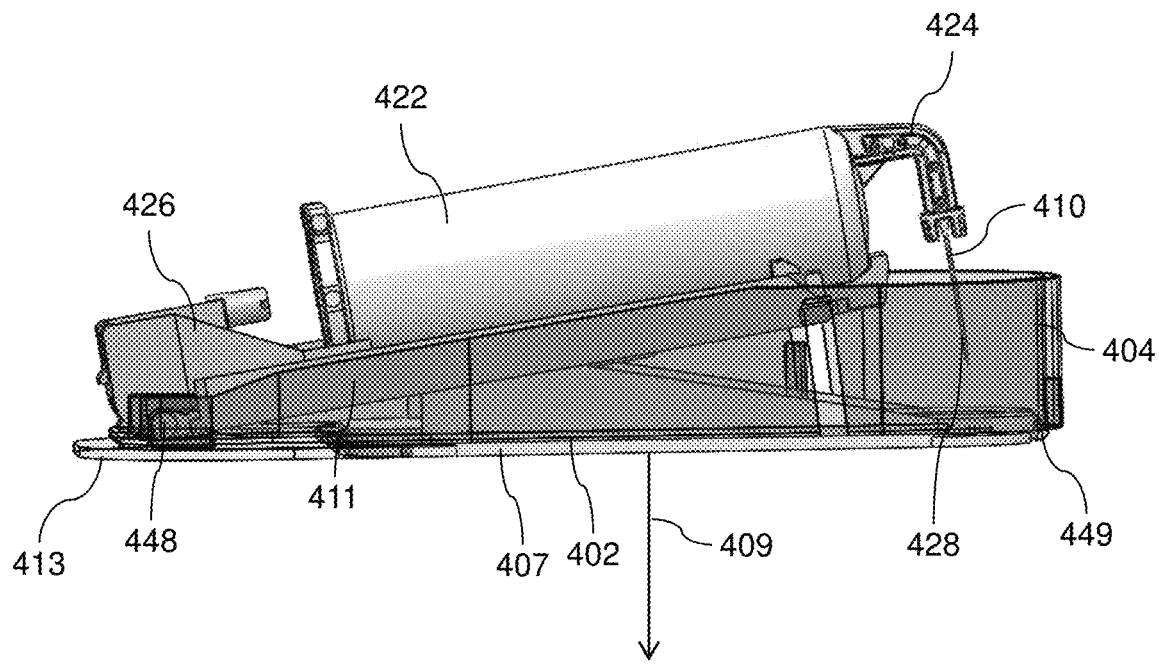
Figure 4C:
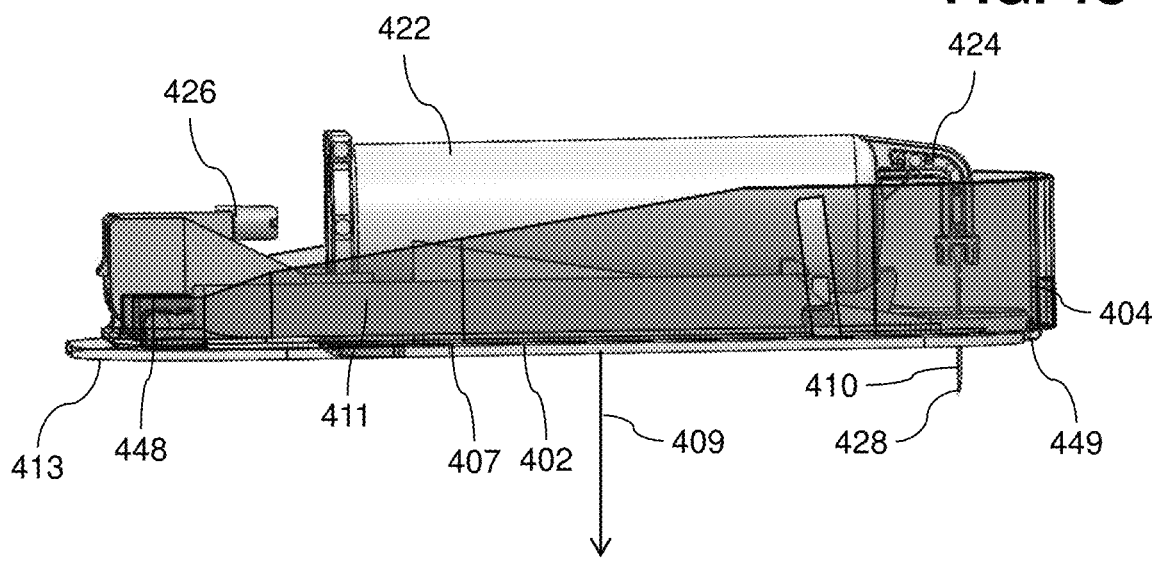
Figure 4D:
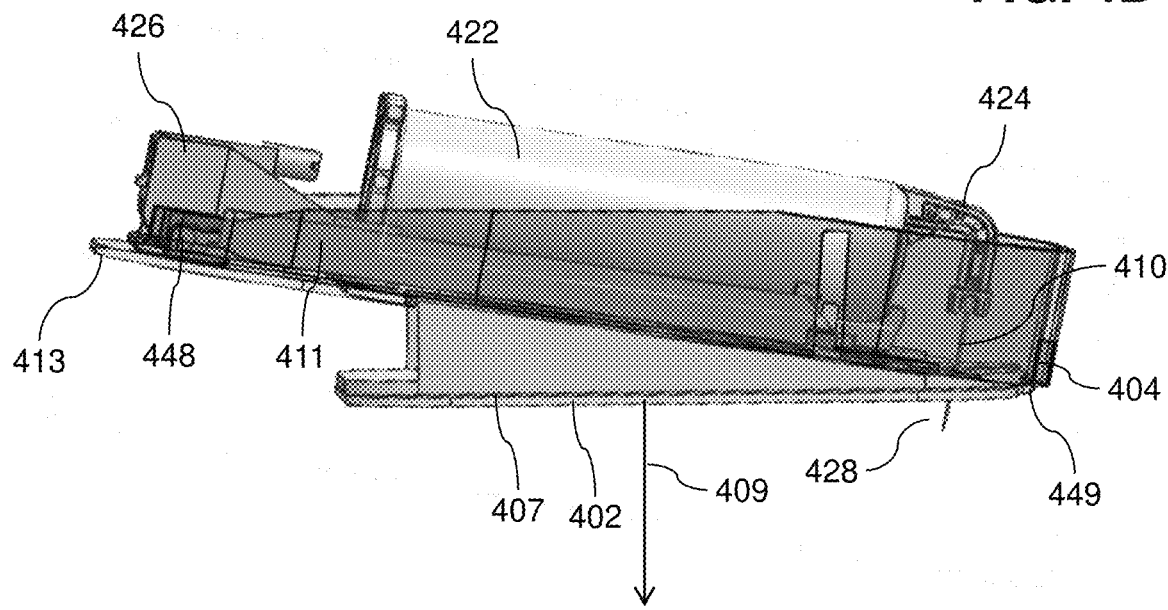

FIGS. 4A-4D are side view illustrations of a four states of an injector in accordance with an embodiment of the present invention. For example, FIG. 4A illustrates the injector in an optional skin detection state. For example, FIG. 4B, illustrates the device in an optional unlocked and/or primed state. For example, FIG. 4C, illustrates the device in an optional active state. For example, FIG. 4D illustrates the device in an optional unlocked removal state. Optionally, needle retraction may return the device from the unlocked removal state to a protected state, for example with the needle positioned as illustrated in FIG. 4A.

In some embodiments, an injector may be supplied with in a locked state. For example, the user may prepare the device by unpacking it, opening the device (for example releasing a base of the device to an extended state). For example, preparing the device may include removing a protective cap and/or removing a protective covering. For example, an adhesive protector may be removed from a skin contact surface on the base of the injector and/or on the body of the injector. Optionally, during unpacking and/or preparing the device, the device may be connected to a power source and/or a computing device (for example a personal computing device of the user). For example, a set of live instructions may be displayed. Optionally preparing the device places the device into a skin detection state. For example, removing the needle cap and/or adhesive protector may extend a base and/or a skin sensor. For example, removing the needle cap and/or adhesive protector may unlock the base and/or the skin sensor for example allowing them to collapse toward the body of the device when attached to an injection site.

FIG. 4A illustrates an injector in an optional skin detection state in accordance with an embodiment of the present invention. For example, in the skin detection state a needle tip may be locked and/or protected inside a body. For example, a needle tip 428 may be surrounded on three sides by a chassis 404 of the body. Optionally, in the skin detection state the needle is locked in the protective state until the injector interacts with and/or is connected to an injection site. For example, the needle may remain in the locked position until at the base of the injector is attached to an injection site and/or the body of the injector is pushed towards the base.

In some embodiments, in the skin detection state, base 402 of the device may be extended away from body of the device. For example, a rear portion of base 402 is pivoted away from chassis 404. Optionally, base 404 includes a skin contact surface 407 on a bottom surface thereof. A vector normal 409 to skin contact surface 407 optionally points away from the body of the device. For example, traveling from surface 407 in the direction of normal 409 may move away from a center of gravity of the body.

Alternatively or additionally traveling from surface 407 in the direction of normal 409 may move away from a nearest point on the body.

In some embodiments, base 402 of the injector may be attached to the skin of a subject (for example at an injection zone) while the device is in the skin detection state.

Optionally after attachment, the chassis 404 is moved towards the base and/or the skin to facilitate activation of the device. For example, facilitating activation of the device may include triggering needle insertion. Alternatively or additionally, facilitating activation of the device may include unlocking an activation switch and/or a needle insertion trigger. Alternatively and/or additionally, attaching the base 402 and moving chassis 404 towards the injection site may be a continuous process. For example, as the user pushes the prepared device onto the skin, first, the contact surface of the base 402 of the device contacts the skin and/or then the chassis 404 is pushed toward the base and/or the skin.

In some embodiments, in the skin detection state, prior to activation, the skin contact surface of the injector may be biased away (for example outward) from the body of the injector. For example, base 402 is biased away from chassis 404. Base 404 is optionally collapsed towards chassis 404 by overcoming the outward biasing force.

Optionally, a retaining force is supplied to retain base 402 in the collapsed state. For example, chassis 404 may include a contact surface 413 and/or an adhesive that retains base 402 in the collapsed state. Optionally, after base 402 is attached to the injection site and/or base 402 collapses into chassis 404, surface 413 contacts and/or attaches to the skin. Attachment of surface 413 to the skin optionally holds base 402 collapsed together with chassis 404. Alternatively or additionally, base 402 may be biased toward chassis 404. Alternatively or additionally, biasing and/or a retaining force may change based on a state of the injector. For example, when drug delivery is completed In some embodiments, the attachment mechanism of the injector may be interlocked to a needle driver and/or a needle extension mechanism. For example, needle 410 is rigidly mounted to an extension 424 of a cartridge. Cartridge 422 is optionally rigidly mounted to a plate 411, which is connected to and/or moves with respect to chassis 404. For example, plate 411 is configured to rotate around a pivot 448. For example, pivot 448 may be fixed in relation to chassis 404 and/or mounting plate 411 may rotate around a location on chassis 404. Movement of plate 411 around pivot 448 optionally causes needle 410 to move longitudinally (for example in an arc trajectory) from a protected position (for example inside the body as illustrated in FIG. 4A) to an extended position (for example with point 428 projecting outward from the body and/or surface 407. Optionally, when base 402 and/or attachment surface 407 are extended away from the body, plate 411 may be locked in a retracted position and/or needle point 428 may be locked in the protected position.

In some embodiments, in the skin detection state, a needle 410 of the injector is substantially perpendicular to contact surface 407 of base 402 (for example needle may range between 0 to 2 degrees and/or 2 to 5 degrees and/or 5 to 10 degrees and/or 10 to 20 degrees and/or 20 to 45 degrees from parallel to normal 409). For example, the orientation of needle 410 to surface 407 may facilitate preparation of the device for example including removal of a needle cap and/or adhesive protector.

Some embodiments may include a plunger driver. For example, a plunger driver may include a telescoping screw assembly 426 and/or a motor and/or a battery and/or a transmission. Alternatively or additionally, a plunger driver may include an expanding gas and/or linear actuator and/or a piston.

FIG. 4B, illustrates the device in an optional unlocked and/or primed state in accordance with an embodiment of the current invention. For example, after attaching the base of the injector to an injection zone of the skin of a subject, the base may be collapsed toward the housing and/or chassis of the injector. For example, a user may collapse the base of the injector towards the body by pushing the body towards the base and/or the skin of the subject.

Optionally, base 402 is interconnected to a lock that keeps needle 410 in the retracted position. For example, collapsing base 402 toward the body may unlock the needle 410 and/or a needle driver. For example, plate 411 may rotate around a pivot 448 to extend needle 410. For example, collapsing base 402 may unlock an activation switch of the injector. Activating the injector optionally triggers a needle driver, to drive needle point 428 into the extended position and/or into the skin of a subject.

FIG. 4C, illustrates the injector in an optional active state. In the active state, a sharp needle tip optionally extends out from the body and/or through the base of the injector. For example, the needle tip may project past skin contact surface 407 into the skin of a subject. In the active state, medicinal substance, for example a drug, is optionally injected through needle 410 into the subject.

In some embodiments, needle tip 428 is inserted into a subject by a rotating needle driver. For example, the needle drive drives plate 411 to rotate around joint 448.

Optionally, in the active state, a longitudinal axis of a barrel of cartridge 422 is substantially parallel to skin contact surface 407 and/or base 402. For example, hinge 448 and hinge 449 are at opposite sides of the injector and/or rotate in the same direction. Alternatively or additionally, two hinges may be on the same side of the device and rotate in opposite directions. Rotation of one hinge may compensate for movement of another hinge such that the relationship between the injector cartridge and the base during the active stage is similar to the relation between the cartridge and the base in the skin detection state (for example before placing the device onto the skin of the user).

For example, in the skin detection state and/or in the active state the base 402 may be parallel to the longitudinal axis of the cartridge 422. For example, in the skin detection state and/or in the active state the base 402 may be perpendicular to the longitudinal axis of needle 410. In some embodiments, in the active state, a needle 410 of the injector is substantially perpendicular to contact surface 407 of base 402 (for example needle may range between 0 to 2 degrees and/or 2 to 5 degrees and/or 5 to 10 degrees and/or 10 to 20 degrees and/or 20 to 45 degrees from parallel to normal 409). For example, the orientation of needle 410 to surface 407 in the active state may be the same or similar to the orientation of needle 410 to surface 407 in the skin detection state. For example the difference in the angle between 410 to surface 407 in the active state to the skin detection state may be range between 0 to 3 degrees and/or between 3 to 10 degrees and/or between 10 to 30 degrees. In some embodiments, base 402 may remain in a collapsed state until the user pulls the body away from the skin. Optionally, an additional skin contact surface may be brought into contact with the skin of the user when the base collapses. For example, an additional contact surface 413 may be on the body of the injector. For example, surface 413 may have an adhesive. Optionally, adhesion of surface 413 to the skin of the subject may inhibit movement of the body away from the skin and/or keep base 402 in the collapsed state.

Alternatively or additionally, there may be a locking mechanism that holds base 402 collapsed during the primed and/or active states of the device.

Alternatively or additionally, the bias of base 402 with respect to the body may depend on the position of base 402 with respect to the body and/or may be depend on the state of the injector.

In some embodiments, a lock may not be released until a threshold force is applied to the body of the device and/or until a section of the body of the device (for example contact surface 413) moves in relation to base 402. For example, contact surface 413 may be biased outward, inward and/or backward and/or interconnected with a lock so that base 402 is released when surface 413 is moved with relation to base 402 and/or the injection zone. Optionally a lock may be released at the end of discharge of a drug and/or upon malfunction of the injector making it easier to trigger needle release. Optionally, releasing the lock may require a pulling the body away from the skin with a particular direction, force, and/or over a minimal time period. For example, unlocking base 402 only for a particular combination of force and/or direction and/or time may avoid base 402 being released unintentionally (for example do to momentum caused by movements of the subject.

FIG. 4D illustrates the device in an optional unlocked removal state. For example, pulling the body of the injector away from base 402 and/or an injection zone of a subject may extend skin surface 407 and/or base 402 away from a body of the injector. Optionally, when the body of the device is distanced away from skin contact surface 407, a needle driver may be triggered to retract needle 410 into a protected location. Optionally triggering retraction may include unlocking a needle release mechanism of the needle driver and/or initiating a needle release mechanism of the needle driver. For example retracting the needle may return device to the configuration of FIG. 4A. Optionally, when needle 410 is retracted, it may be locked. Locking needle 410 in the retracted configuration may place the device into a protected state.

Optionally, after needle retraction, needle 410 may be inhibited from being reexposed. For example, the needle exposure process described above with respect to FIGS. 4A, 4B and/or 4C may be blocked when needle 410 is retracted.

Optionally, base 402 is biased away from the body. Biasing optionally extends base 402 away from the body whenever there is no force preventing extension. For example, base 402 may extend away from the body when surface 413 is separated from the skin regardless of whether the body is pulled away from base 402 or the separation is due to other factors (for example peeling the adhesive from the skin). Alternatively or additionally, base 402 may be biased toward the body. For example, extension of base 402 may be due to adhesive forces pulling contact surface 407 towards the injection site as the body is pulled away from the injection site.

Figure 5A:
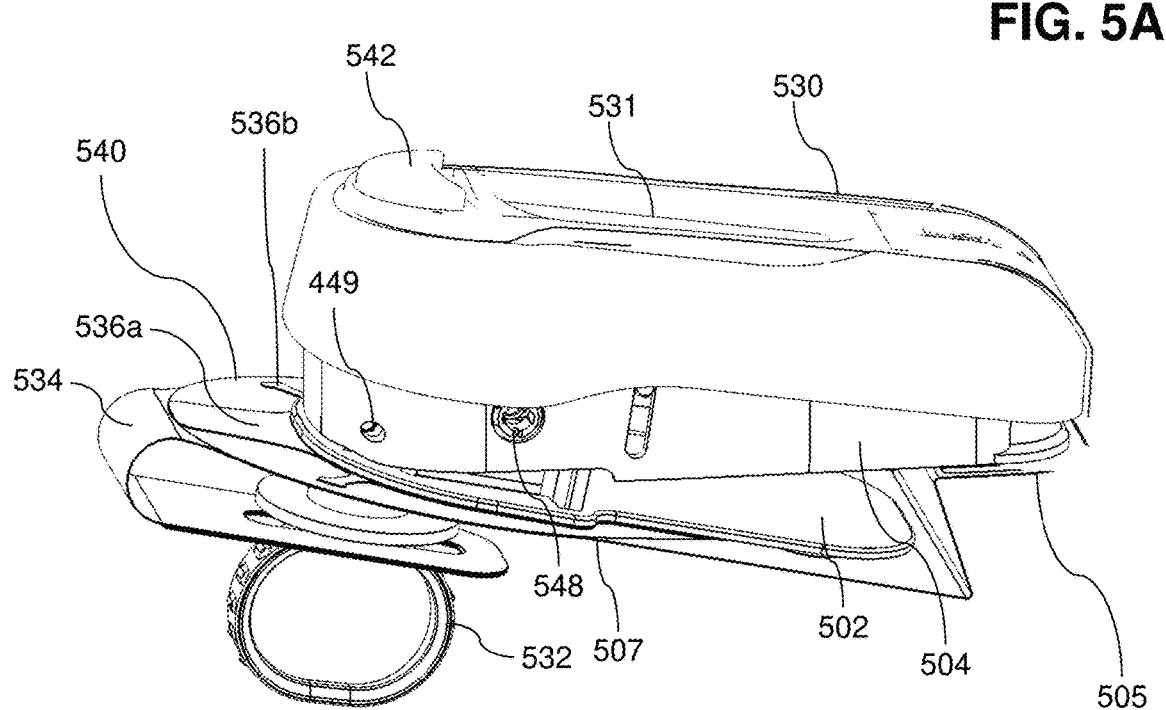
FIGS. 5A and 5B are a perspective view illustrations of an injector in accordance with an embodiment of the present invention.
Figure 5B:
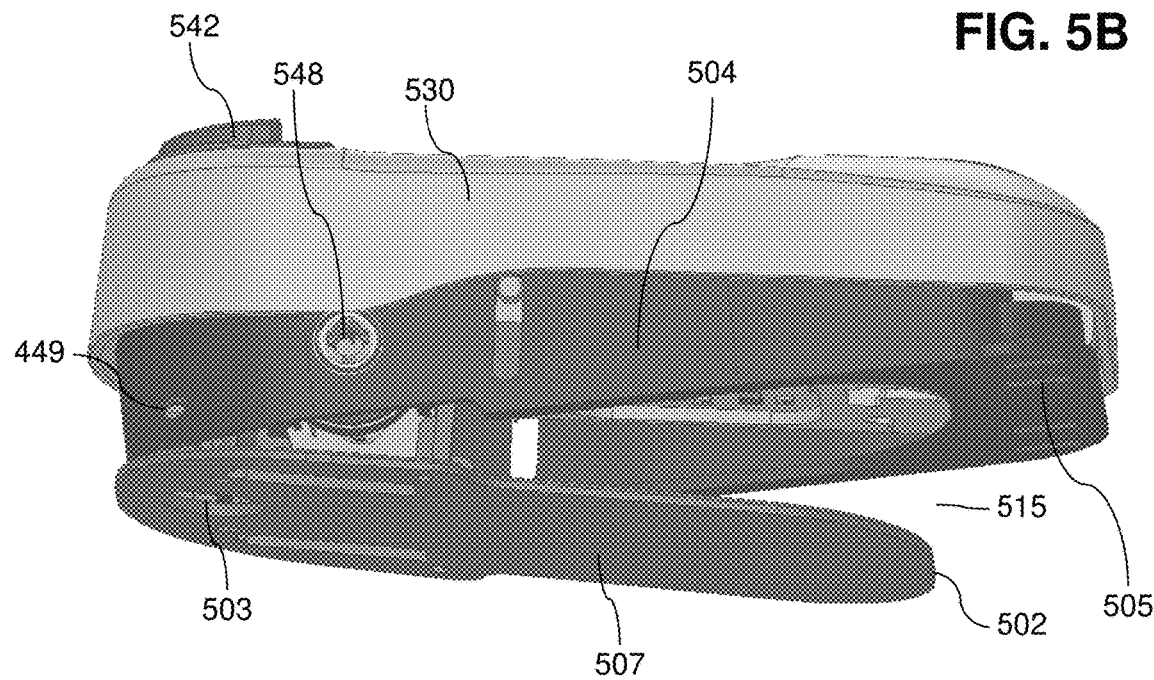

FIGS. 5A and 5B are a perspective view illustrations of an injector in accordance with an embodiment of the present invention. In some embodiments, an injector includes an extendable base. The extendable base may be interconnected to a needle driver such that collapse and/or extension of the base facilitates and/or triggers needle insertion and/or retraction.

Optionally the base includes a skin contact surface. For example, the skin contact surface may include an adhesive. For example, the adhesive may be configured to adhere the contact surface to the skin of a subject, for example near and/or surrounding a needle insertion site. The injector is optionally configured to encourage intuitive placement and/or removal of the device and/or intuitive triggering of needle insertion and/or retraction.

FIG. 5A illustrates an injector with an adhesive and needle cover in accordance with an embodiment of the current invention. In some embodiments, an injector includes a body and a base 502 movably mounted to the body. For example, a body may include a housing 530 and a chassis 504. Base 502 is optionally movably attached to chassis 504. For example, base 502 moves rotationally around a pivot 449 connected to chassis 504.

In some embodiments, features on the injector encourage intuitive understanding of placement of the injector on the skin. For example, one or more skin contact surfaces 507, 505 of the injector may include an adhesive 540. Adhesive 540 may be covered with an adhesive protector liner 534. Preparing the injector for use optionally includes peeling one or more adhesive liners 534 off of adhesive 540. Peeling adhesive liners 534 from adhesive 540 clues the user to the need to place and/or stick surfaces 507 and 505 to the skin. Optionally, in the skin detecting state contact surfaces 505 and 507 may not form a continuous surface. For example, there may be a gap. For example, the gap may range between 0.1 and 0.3 cm and/or between 0.3 and 0.6 cm and/or between 0.6 to 1.2 cm and/or between 1.2 to 2.4 cm and/or greater than 2.4 cm.

A user may intuitively understand that he should place the protruding contact surface 507 against the skin and then push against the body to collapse gap 515 and bring contact surface 505 into contact with the skin. In some embodiments a single adhesive liner 534 covers multiple adhesive areas (for example contact surfaces 507 and/or 505). Alternatively or additional, separate adhesive areas may be covered by separate adhesive liners. In some embodiments, a single handle 532 is used to prepare multiple aspects of the injector (for example to remove adhesive liners from contact surfaces 505 and/or 507 and/or to remove the needle cover). Alternatively or additional, separate handles may be used to prepare separate aspects of the injector.

In some embodiments, an injector includes an adhesive covering a skin contact surface. For example, an adhesive 540 may cover a first skin contact surface 507 on base 502. A separate section of adhesive optionally covers a second skin contact surface 505 on the body (for example on a rear portion of chassis 504). Optionally the adhesive may overhang beyond the edge of base 502 and/or chassis 504. For example, an adhesive skirt may overhang beyond the front and sides of base 502. Optionally the overhang is strengthened by a stiffener 536a, 536b.

In some embodiments, a handle is included for intuitive preparation of the injector. For example, a pull ring handle 532 is connected to a needle cover and/or adhesive liner 534. Handle 532 optionally supplies an intuitive clue to a user that he should remove the needle cover and/or adhesive liner 534 before placing contact surface 507 against the skin. Optionally, the injector includes a lock preventing priming of the injector until handle 532 has been moved (for example until handle 532 has been pulled away from the injector along with the needle cap and/or adhesive liner 534). For example, a skin sensor may be covered and/or locked in a disengaged state (for example extended away from the body) and/or example an activation switch (for example a button 542) may be locked in an inactivated position until handle 534 is pulled away from the injector. In some embodiments, different preparation activities are connected such that a user can perform one action and prepare multiple parts of the injector. For example, the needle cover may connect to an adhesive liner 534 that covers both skin contact surface 507 on base 502 and skin contact surface 505 on housing 530.

Optionally peeling off adhesive liner 534 from both contact surfaces 505 and 507 and removing the needle cover (for example by pulling the needle cover through an opening 503 in base 502) are achieved with one intuitive act of pulling pull ring 532 away from base 502. Alternatively or additionally, a separate adhesive protector may be supplied for each contact surface 505, 507 and/or removing the needle cover may be independent of removing an adhesive protector.

In some embodiments, features on the body facilitate intuitive placement of the injector. For example, the base that is placed on the skin may be the largest flat surface of the injector. Optionally, the top of the injector (opposite the skin contact surface may include a user interface (for example a switch for example button 542 and/or a display for example window 531). A user may intuitively understand that a display and/or button will not be attached against the skin. Optionally sides of the injector that are not placed against the skin will be generally non-flat (e.g. rounded and/or include protrusions and/or indentations).

In some embodiments, opening 503 in base 502 of the device may be large enough to insert and/or remove a sterile needle cover. For example, the width of the opening may range between 1 mm to 2 mm and/or between 2 mm to 4 mm and/or between 4 mm to 10 mm.

Figure 6A:
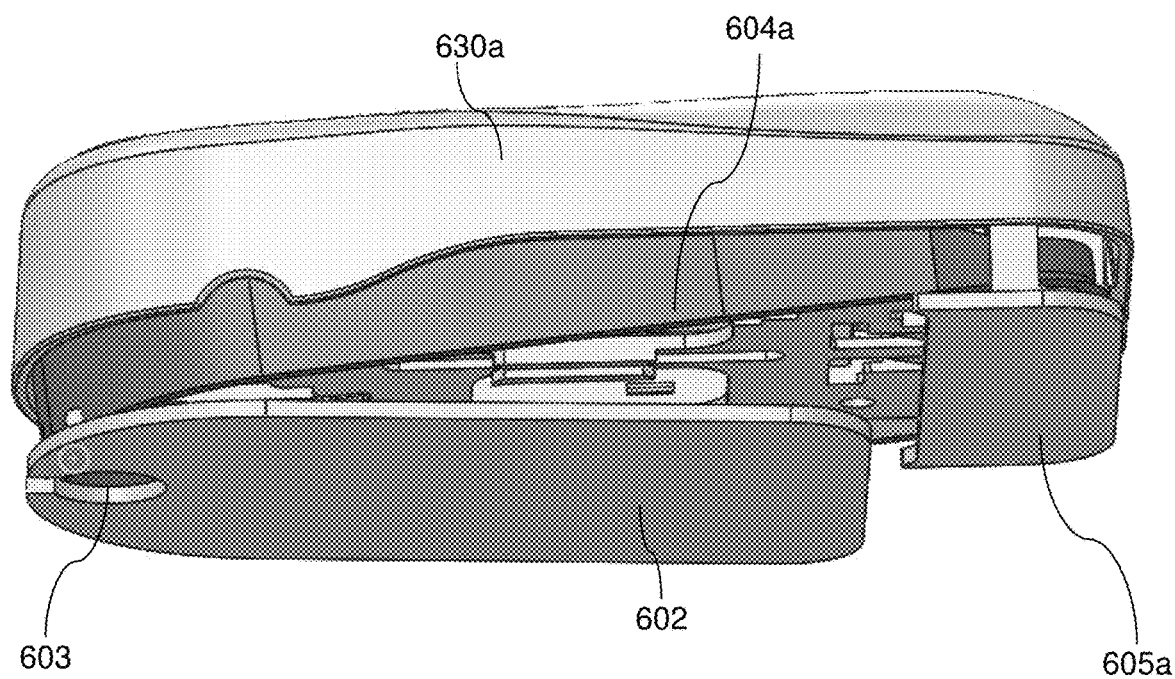
FIGS. 6A-6D are perspective view illustrations of injectors including an insertion and/or retraction mechanism in accordance with embodiments of the present invention.

FIG. 6A is a perspective view of an embodiment of an injector in accordance with an embodiment of the current invention. In some embodiments, an outer housing 630a of an injector includes retaining mechanism, for example a skin contact surface 605a. Optionally, surface 605a includes an adhesive for attaching to the skin of a subject. For example, when the device is active adhesion between surface 605a and the skin of the subject may retain body on the skin and/or retain a base 602 of the injector in a collapsed position next to a chassis 604a.

Figure 6B:
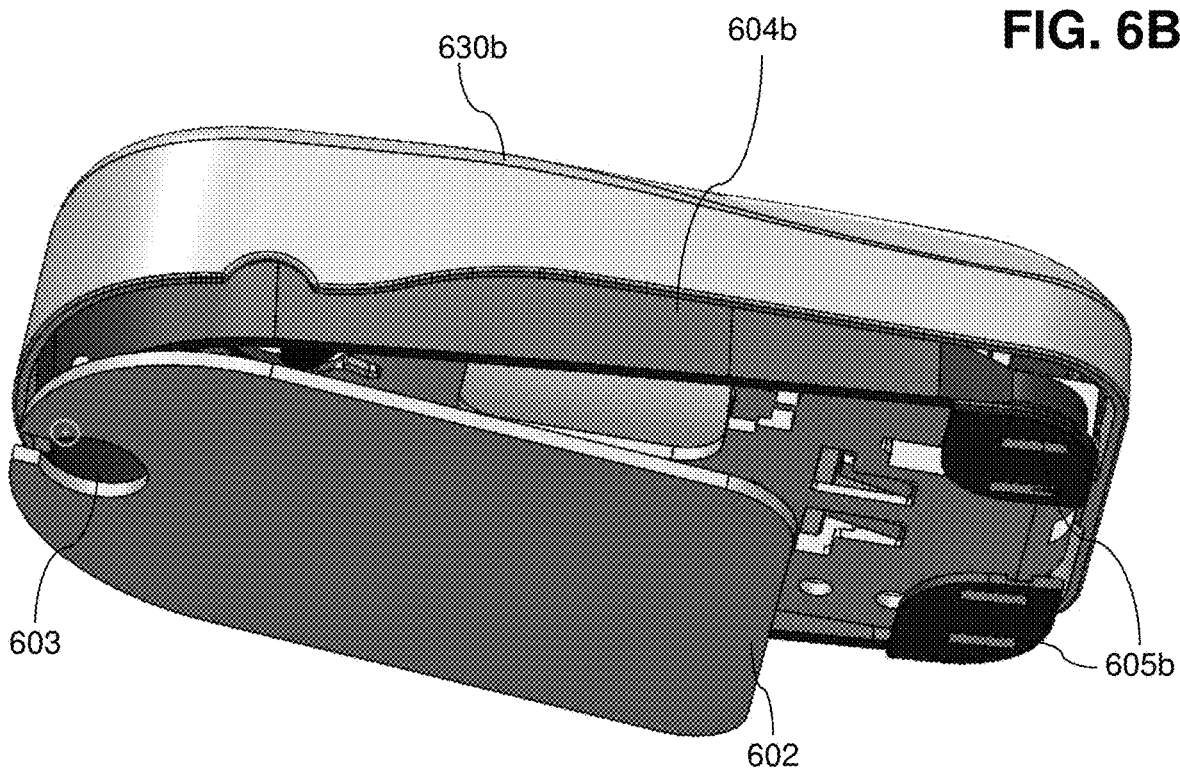

FIG. 6B is a perspective view of an embodiment of an injector in accordance with an embodiment of the current invention. In some embodiments, a chassis 604*a* of an injector includes retaining mechanism, for example a skin contact surface 605*b*.

Optionally, surface 605*b* includes an adhesive for attaching to the skin of a subject. For example, when the device is active, adhesion between surface 605*b* and the skin of the subject may retain the body on the skin and/or retain a base 602 of the injector in a collapsed position next to chassis 604*b*.

In some embodiments, when surface 605*a* or 605*b* is pulled away from the skin of the user, base 602 may move away from chassis 604*a* or 604*b*, causing needle retraction.

In some embodiments, base 602 includes a skin contact surface and/or an adhesive. For example, the adhesive on base 602 may be strong enough to support the injector on an injection site. Optionally, base 602 includes a needle opening 603. For example, when the injector is in an active state, a needle may protrude through opening 603 into an injection site. Optionally, opening 603 is large enough to insert and/or remove a needle cover from a needle when the needle is retracted behind base 603 for example as illustrated in FIGS. 6A and 6B. Optionally, a retaining mechanism may include multiple parts and/or mechanisms and/or attachment surfaces.

In some embodiments base 602 is attached to housing 630*a*, 630*b* and/or chassis 604*a*, 604*b* via a hinge. For example, the hinge may be near needle hole 603 (e.g. nearer to the front end of the device with the needle hole than the rear end of the device opposite the needle hole). For example, movement of the needle hole may be less than movement of the opposite end of base 602 when base 602 is moved away from chassis 604*a*, 604*b*. For example, the location of the center of mass of the needle hole may range between 0 to 10% of the distance between the hinge and the far end of the base and/or between 10 to 30% of the distance between the hinge and the far end of the base and/or between 30 to 50% of the distance between the hinge and the far end of the base and/or between 50 to 80% of the distance between the hinge and the far end of the base and/or FIGS. 6C and 6D are perspective views of embodiments of an injector at the point of needle retraction in accordance with an embodiment of the current invention.

In some embodiments, needle retraction occurs when the skin contact surface 505 of the chassis 504 and/or on a body of the pharmaceutical delivery device lifts off a skin 693 of a subject. Alternately or additionally, in some embodiments the needle retracts while a skin contact surface 505 of the chassis and/or body of the injector is still connected to the skin. For example, the relative movement between the skin contact surfaces of the based 502 and the skin contact surface of the chassis 505 that triggers needle retraction may be more than and/or less than the distance that the skin can stretch to compensate for such movements. For example, the distance of relative movement between the skin contact surface on the base and the skin contact surface on the chassis and/or body of the injector at their closest points may range between 0 to 0.3 mm and/or between 0.3 to 1 mm and/or between 1 mm to 3 mm and/or between 3 mm to 10 mm and/or between 10 mm to 30 mm. Alternatively or additionally, the base may pivot with respect to the body and/or chassis of the injector at an angle of between 0 to 2 degrees and/or between 2 to 6 degrees and/or between 6 to 12 degrees and/or between 12 to 24 degrees and/or between 24 to 45 degrees when the needle retracts.

Figure 6C:
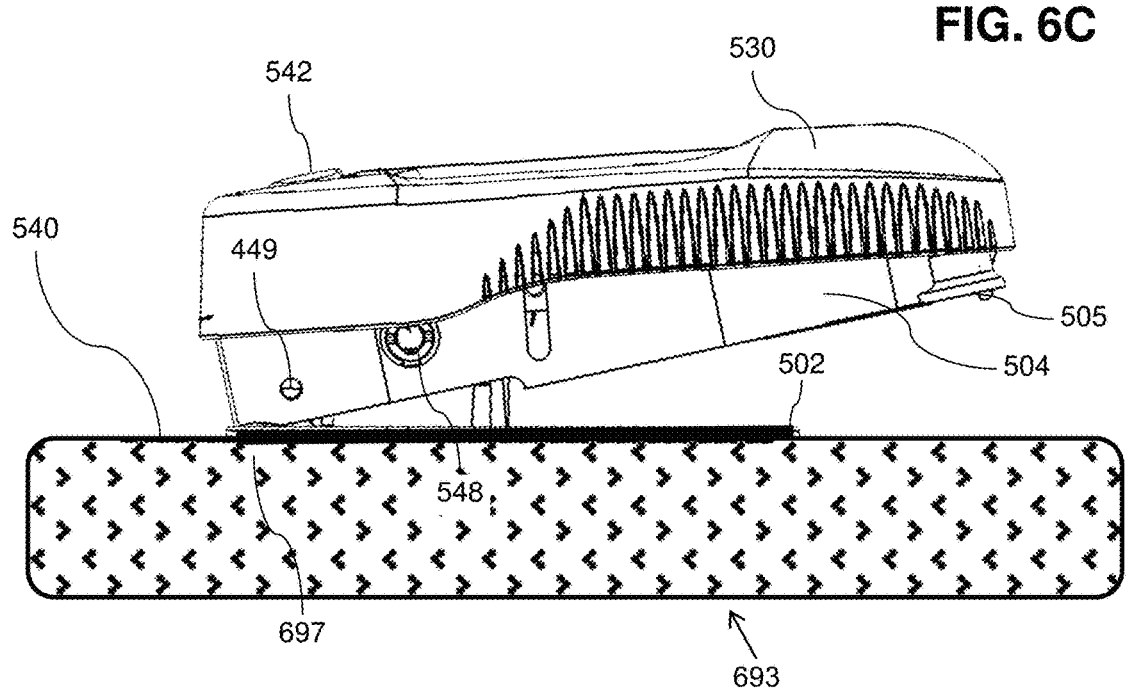
Figure 6D:
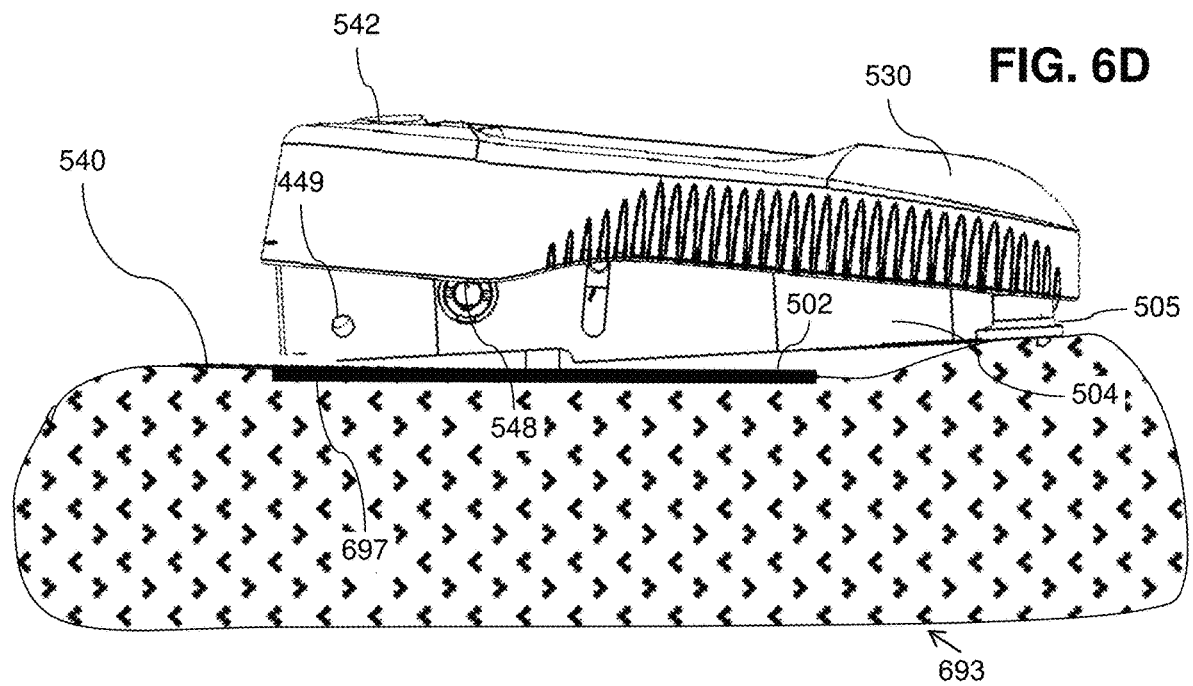

FIG. 6C illustrates embodiment the needle retraction mechanism in which needle retraction occurs when the bass 502 is fully distanced from chassis 504 and/or the skin contact surface 505 of chassis 504 is disconnected from the skin 693 of a subject. For example, the distance between base 502 and chassis 504 at which needle retract occurs may be large enough that while base 502 remains adhered on skin 693, the skin contact surface 505 of chassis 504 raises up off the skin surface. Optionally, when the needle retracts, base 502 is still adhered to the skin 693 around an injection site 697.

For example, in an embodiment in an embodiment where contact surface 505 remains in contact with the skin while the needle retracts, needle retraction may occur when base 502 pivots outward less than 3 degrees and/or less than 5 degrees and/or less than 10 degrees. For example, in an embodiment in an embodiment where contact surface 505 remains in contact with the skin while the needle retracts, needle retraction may occur when the closes points between base 502 and contact surface 505 move between 0 to 0.3 mm and/or between 0.3 to 1 mm and/or between 1 mm to 3 mm and/or between 3 mm to 5 mm relative to one another.

FIG. 6D illustrates an embodiment of an injector where both the skin contact surface of base 502 and the skin contact surface 505 of the chassis 504 remain adhered to the skin when the needle retracts. For example, the needle may retract when the base 502 is only slightly moved with respect to the chassis 504. For example, the relative movement of the skin contact surface on the base 502 and the skin contact surface 505 on the chassis 504 may be small enough when the needle retracts that elasticity of the skin compensates. For example, in an embodiment in an embodiment where contact surface 505 is separated from the skin while the needle retracts, needle retraction may occur when base 502 pivots outward between 5 to 10 degrees and/or between 10 to 20 degrees and/or between 20 to 45 degrees. For example, in an embodiment in an embodiment where contact surface 505 remains in contact with the skin while the needle retracts, needle retraction may occur when the closes points between base 502 and contact surface 505 move between 1 mm to 3 mm and/or between 3 mm to 5 mm and/or between 3 mm to 5 mm and/or between 5 mm to 15 mm relative to one another.

FIGS. 7A-7J are perspective and cut away views of various states of an injector including an exemplary needle insertion mechanism and/or a needle retraction mechanism in accordance with an embodiment of the present invention. Optionally, needle retraction and/or insertion may be driven by a spiral torsion spring and/or a rotary motion drive. For example, movement of the spring may be limited according to a position of the base of the device.

Figure 7A:
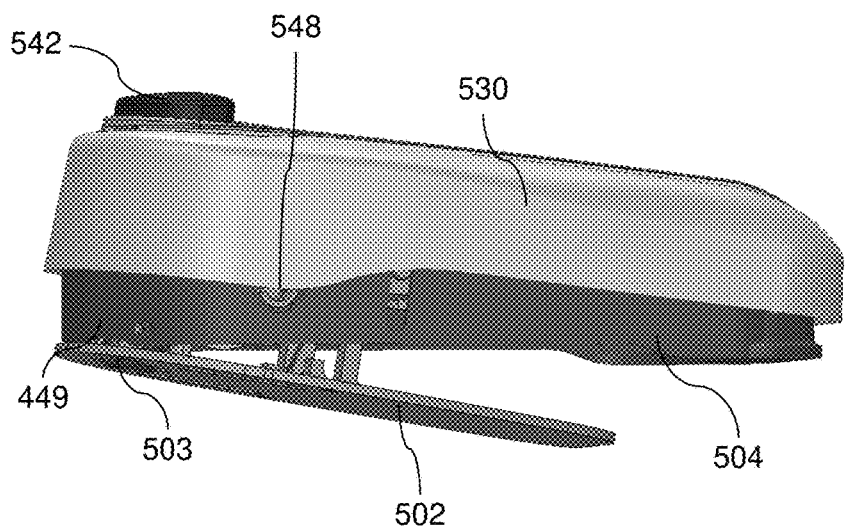
Figure 7B:
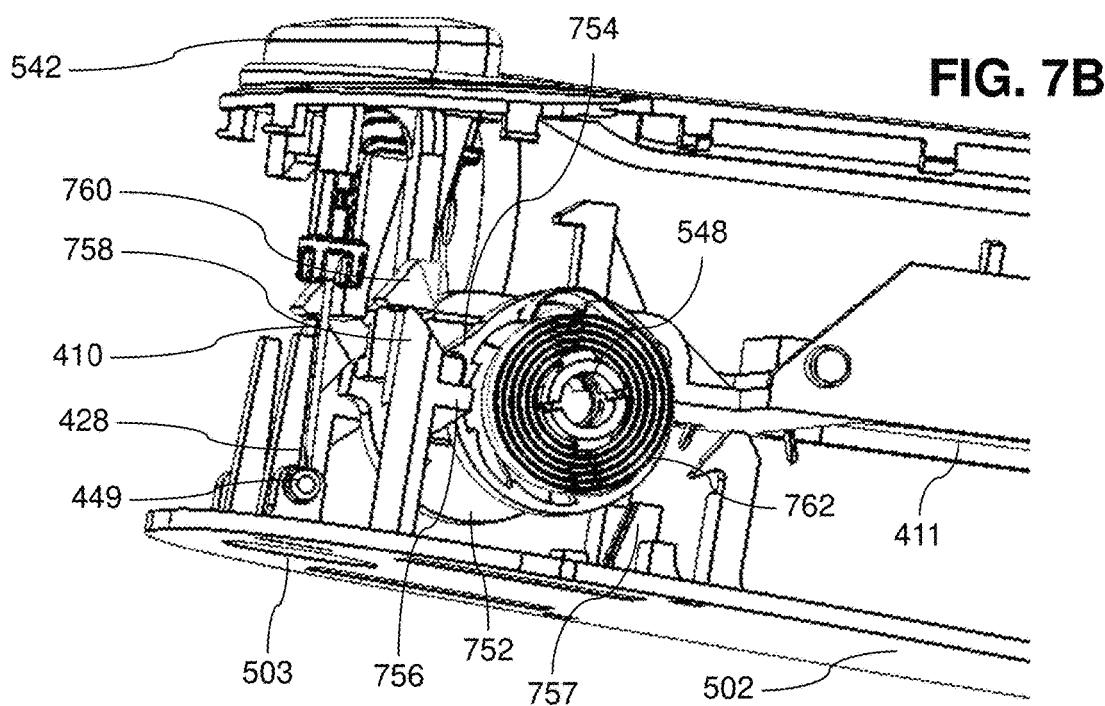

FIGS. 7A and 7B are a perspective and cut away illustrations of a drug delivery device ready to be placed on the skin of a subject in accordance with an embodiment of the current invention. Some external features of the device of FIG. 7A have been describe for example in the description of FIGS. 5A and 5B.

FIG. 7B illustrates a cut away view of an injector in a ready state in accordance with an embodiment of the current invention. In some embodiments, insertion and/or retraction of a needle 410 is driven by a driving wheel 752. In the ready state, drive wheel 752 optionally holds needle 410 in a retracted state. For example, in the ready state, an interference element 756 connected to base 502 of the injector may block movement of a spur 754 on wheel 752 and/or inhibit extension of needle 410.

Optionally wheel 752 rotates around an axis 548.

In some embodiments, a stored energy source impels drive wheel 752. For example, a stored energy source may include a spiral torsion spring 762.

In some embodiments, in the ready state, base 502 may interfere with pushing an activation button 542. For example, while base 502 is extended away from the chassis 504 of the injector, interference element 756 may block movement of an extension 760 of button 542. Optionally, opening 503 is near the pivot 449 of base 502 and/or opening 503 is aligned with needle 410 while base 502 is in the extended position. For example, alignment of needle 410 and opening 503 may allow a needle cover to extend through opening 503.

Optionally base 502 includes a biasing member. For example, member includes an elastic element that is deformed when base 502 is collapsed into chassis 504 and/or forces base 502 into the extended position. For example, member includes a leaf spring that is pushed up against a front wall of chassis 504 when base 502 is collapsed. Alternatively or alternatively, a biasing member may include a coil spring and/or a torsion spring and/or a cushioning element.

Figure 7C:
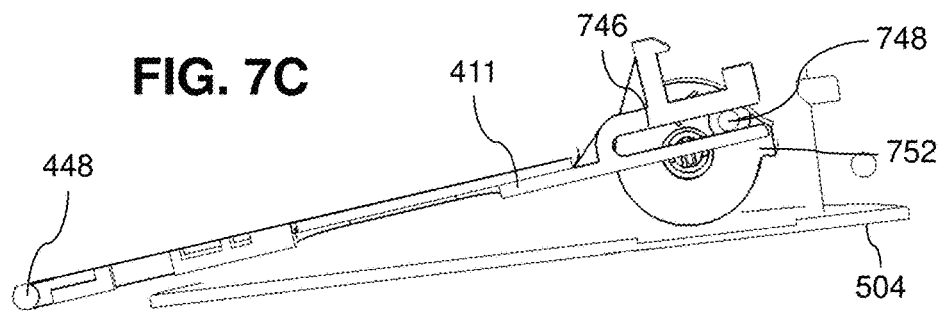

FIG. 7C illustrates a cut away view of a cam drive of an injector in a primed state in accordance with an embodiment of the current invention. In some embodiments, movement of a needle is driven by a rotary drive cam structure including a driving wheel 752 and/or a pin 748 and/or a track 746. For example, a needle assembly may be mounted on a mounting plate 411. Optionally, mounting plate 411 rotates around a pivot 448. Optionally, in the initial needle retracted state, driving wheel 752 is positioned with pin 748 distanced from a skin contact surface of the injector (for example in the primed state (when base 502 is optionally collapsed into chassis 504)), the skin contact surface may include an outer surface of base 502 and chassis 504.

Optionally, in the primed state, pin 748 holds track 746 and/or mounting plate 411 and/or needle tip 428 in a retracted position behind the skin contact surface.

FIG. 7C' illustrates a perspective external view of an injector in a primed state in accordance with an embodiment of the current invention. Optionally in the primed state, base 502 is collapsed against chassis 504. For example, collapsing may be caused by pushing the injector against an injection site. For example, base 502 and the bottom surface of chassis 504 may be held flush against the surface of the injection site. For example, base 502 may be attached to the injection site by an adhesive 540. For example, a skirt of adhesive 540 may by unattached to base 502.

FIG. 7D illustrates a cutaway view of an injector in a primed state in accordance with an embodiment of the current invention. In some embodiments, in the primed state, element 758 may no longer inhibit pushing of activation button 542. For example, element 758 may be positioned such that a sloped surface of extension 760 of button 542 contacts element 758 such that pushing button 542 pushes element 758 out of the way of extension 760. Optionally, pushing button 542 pushes element 758 out of the way of spur 754 of wheel 752 and/or frees wheel 752 to turn to its active position and/or drive needle tip 428 out through opening 503 for example as illustrated in FIG. 7E.

Alternatively or additionally, movement of base 502 may directly cause element 758 to move out of the way of spur 754 of wheel 752. For example, of needle tip 428 may extend immediately upon collapse of base 402 toward chassis 404 without the user pushing a button. Alternatively or additionally, needle tip 428 may be extended manually, for example, by a force of the user pushing housing 530 and/or a button 542 towards the injection site, for example, needle extension may not be powered by a stored energy source in the injector.

FIG. 7E is a cutaway view of a needle driver in an activated state in accordance with an embodiment of the current invention. Optionally in the active state, wheel 752 has been rotated by spring 762 until pin 748 is positioned close to the skin contact surface of base 502 and/or chassis 504. Optionally, pin 748 drives track 746 toward the skin contact surface and/or drives mounting plate 411 towards the skin contact surfaces and/or drives needle tip 428 out opening 503 to an extended position (for example as illustrated in FIGS. 7E' and 7F).

FIG. 7E' is an exterior perspective view of an injector in an active state in accordance with an embodiment of the current invention. Optionally, in the active state needle tip 428 is extended out opening 503. For example, base 402 is collapsed into chassis 404 and/or housing 530 such that skin contact surfaces of base 402 and/or chassis 404 and/or housing 530 are flush. For example, the contact surfaces may be in contact with and/or adhere to a skin surface of the user.

FIG. 7F illustrates a cutaway view of a needle driver and base in an active state in accordance with an embodiment of the current invention. For example, in the active state an interference element 757 on base 502 may block spur 754 and/or inhibit further rotation of wheel 752. Further rotation of wheel 752 would move pin 748, plate 411 and/or needle tip 428 upward away from the skin contact surfaces. Blocking further rotation optionally, locks pin 748, plate 411 and/or needle tip 428 in the extended position.

Figure 7G:
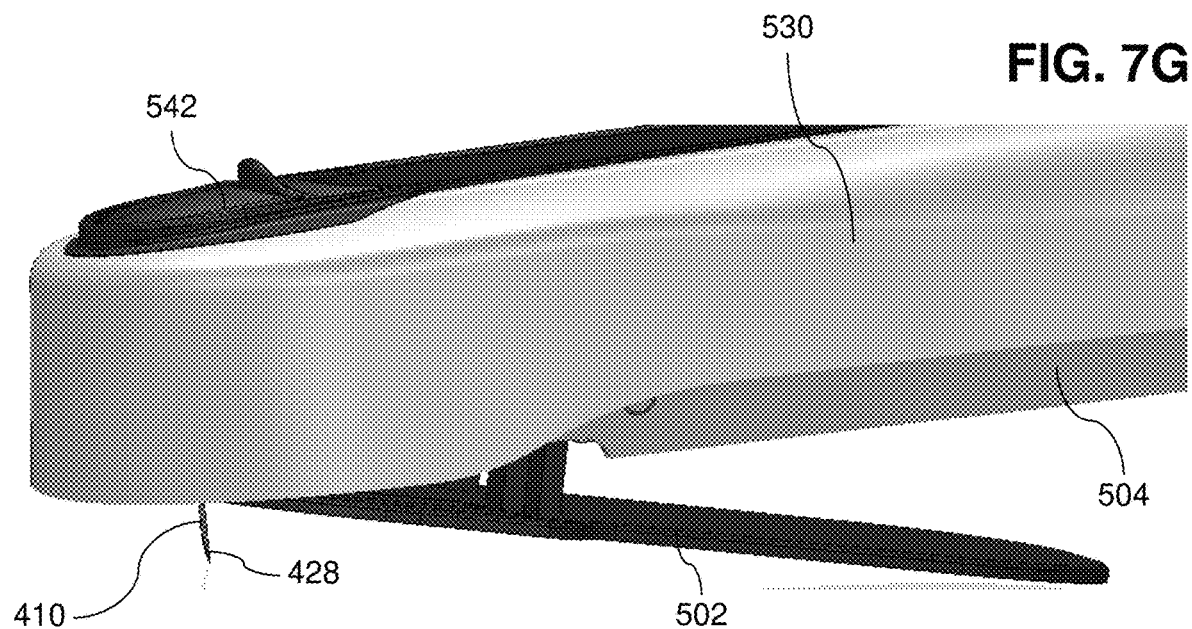

FIG. 7G is an external perspective view of an injector in the process of removal from an injection site in accordance with an embodiment of the current invention. In some embodiments, pulling housing 530 away from an injection zone, causes base 502 to extend outward from chassis 504. For example, base 502 rotates around pivot 449 with respect to chassis 504.

In some embodiments, in the primed state, opening 503 is aligned with needle 410 such that movement of mounting plate 411 towards chassis 504 and/or base 502 extends needle tip 428 out opening 503.

Figure 7H:
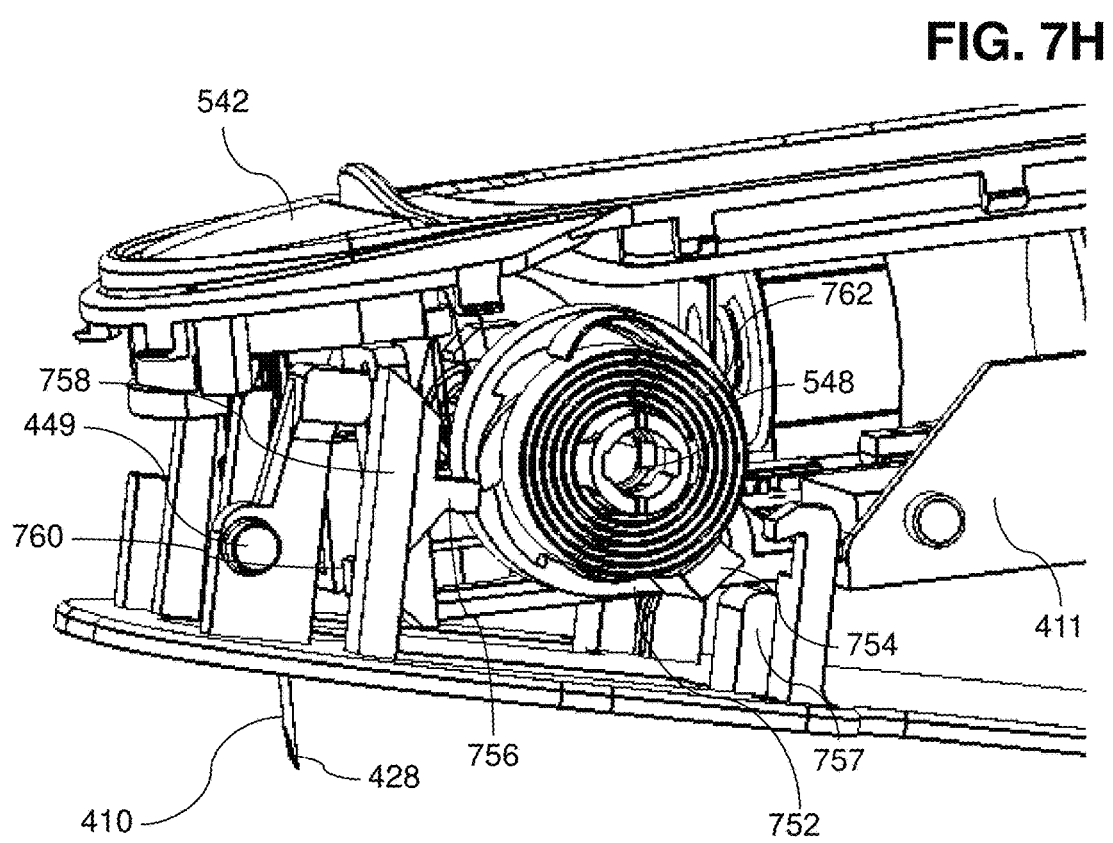

FIG. 7H is a cutaway view of a needle driver of an injector in the process of removal from an injection site in accordance with an embodiment of the current invention. Optionally, moving base 502 away from chassis 504 disengages interference element 757 from spur 754. For example, once freed of interference element 757, wheel 752 turns a half rotation moving pin upward to a position distanced from the skin contact surface of plate 411 and/or chassis 504 and/or base 502. Moving pin away from the skin contact surfaces optionally rotates plate 411 away from chassis 504 and/or retracts needle tip 428 through opening 503 and/or up behind the skin contact surface of base 502 and/or chassis 504 and/or body 530.

Figure 7I:
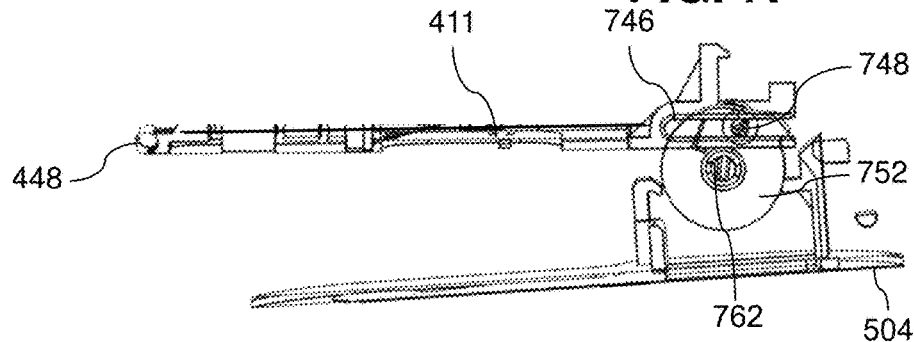
Figure 7I:
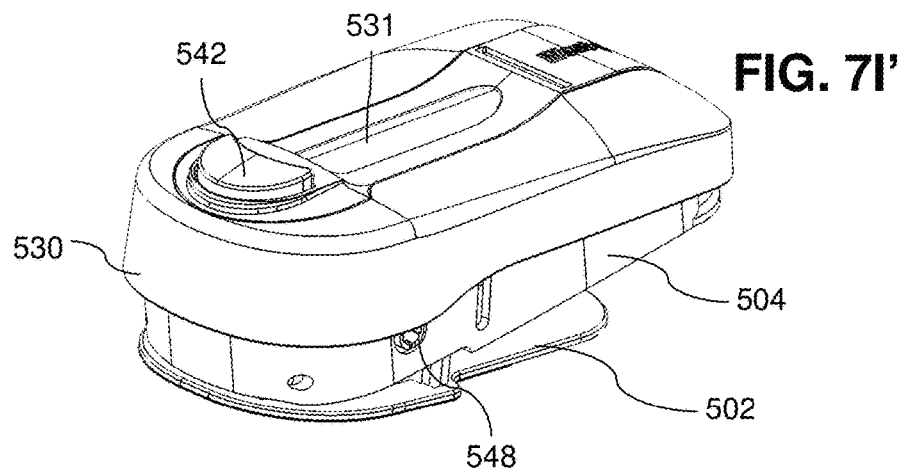
Figure 7J:
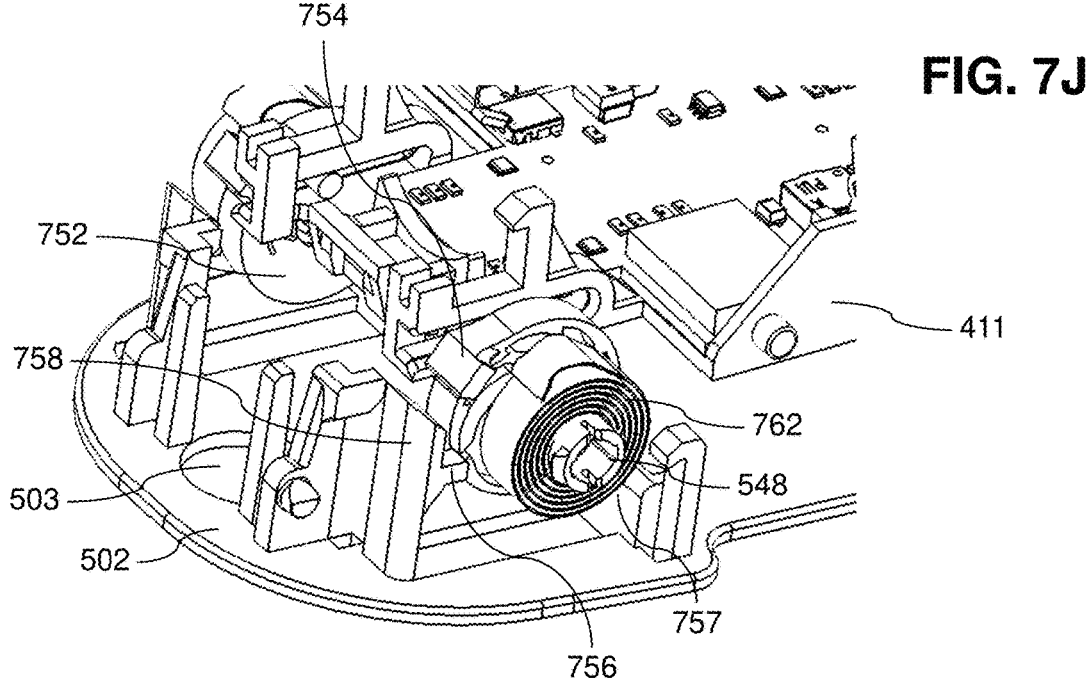

FIG. 7I illustrates a driver of an injector in a protected state in accordance with an embodiment of the current invention. Optionally, during retraction, wheel 752 is rotated by spring 762 until pin 748 just passes the point furthest from the skin contact surfaces of base 502. Optionally, during retraction, wheel 752 is rotated by spring 762 until pin 748 almost reaches its preinjection position (for example as illustrated in FIG. 7C). For example, a stop prevents further movement of wheel 752. Optionally, needle tip 428 is locked retracted by the stop of wheel 752 (preventing wheel 752 from going forward) and/or by spring 762 (prevent wheel from going backward) and/or because a downward force pushed wheel 752 into the stop. In some embodiments, needle 410 remains aligned with opening 503 after retraction. For example, locking of needle 410 in the retracted position prevents a stick hazard regardless of the alignment between needle 410 and opening 503.

FIGS. 7I' and 7J illustrate an external perspective view and a cutaway internal view respectively of an injector in a protected state in accordance with an embodiment of the current invention.

In some embodiments, base 502 is biased outwards, away from chassis 504. For example, even if somehow base 502 is peeled off the injection site without opening, biasing will cause base 502 to open and/or retract needle tip 428. Alternatively or additionally, a base may rotate freely without biasing and/or the base may be biased inward (toward the chassis). For example, when the body is pulled away from the injection site, the adhesive may pull the base away from the body and/or cause needle retraction. Alternatively or additionally, the needle may not retract with respect to the body. For example, when the base extends away from the body it may extend outward past the needle tip and/or shield the needle tip, for example to prevent a stick hazard.

Adhesive Structure

Figure 8:
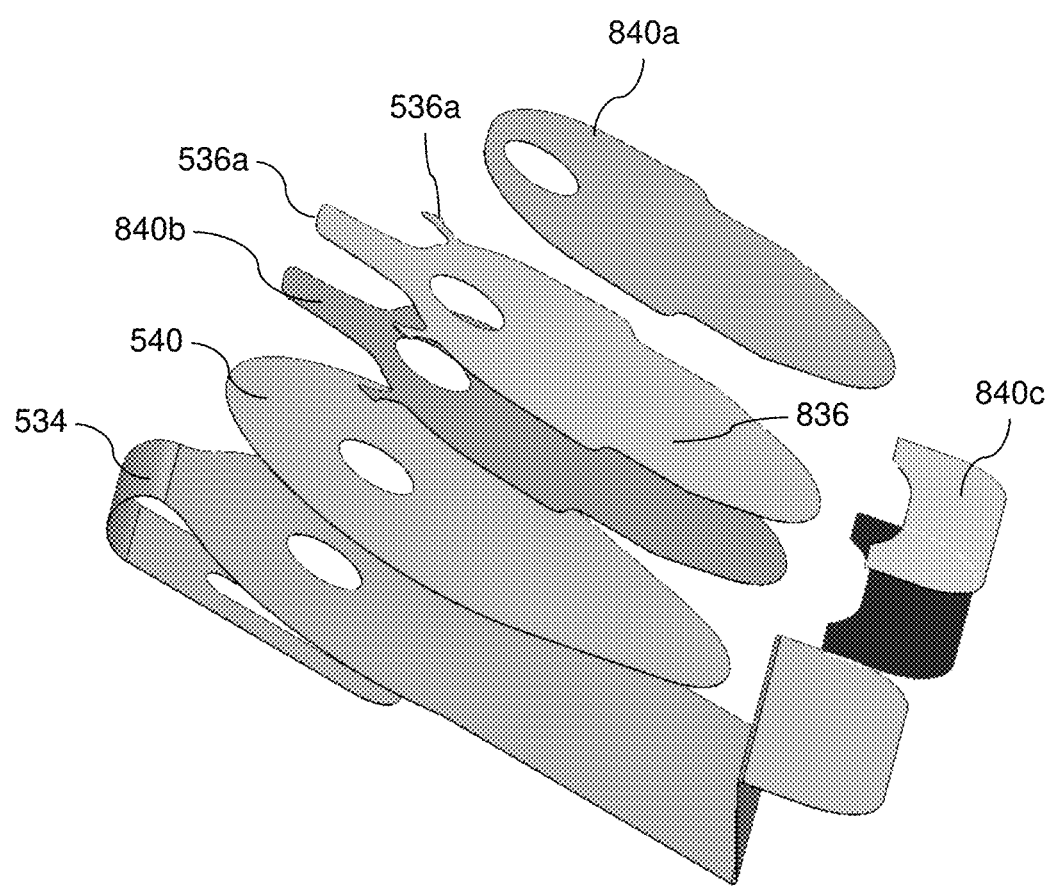
FIG. 8 is an exploded view of an adhesive structure in accordance with an embodiment of the present invention.

FIG. 8 is an exploded view of an adhesive structure in accordance with an embodiment of the present invention. Optionally, skin adhesive 540 includes a flexible substrate with an adhesive on one side. An optional adhesive layer 840b connects the flexible substrate of adhesive 840b to a stiffener 836. Part of stiffener 836 is attached to base 502 by an adhesive layer 840a. Optionally, part of stiffener 836 and/or part of the substrate of adhesive 540 forms a skirt. For example, part of the skirt may overhang beyond base 502 and/or part of the skirt may underlie base 502, but not be attached thereto. In some embodiments, a second adhesive is connected to the housing and/or chassis of the device. For example, a double sided adhesive 840c may be attached to contact surface 505 of chassis 504. Optionally a protective liner 534 covers skin adhesives 540 and/or 840c. In some embodiments, liner 534 is peeled off before use of the injector. Optionally liner 534 may be interconnected to a sterile needle cap.

Optionally the needle cap and liner 534 may removed and peeled off together.

Alternatively or additionally, an adhesive structure may have a different number of parts and/or layers.

Figure 9A:
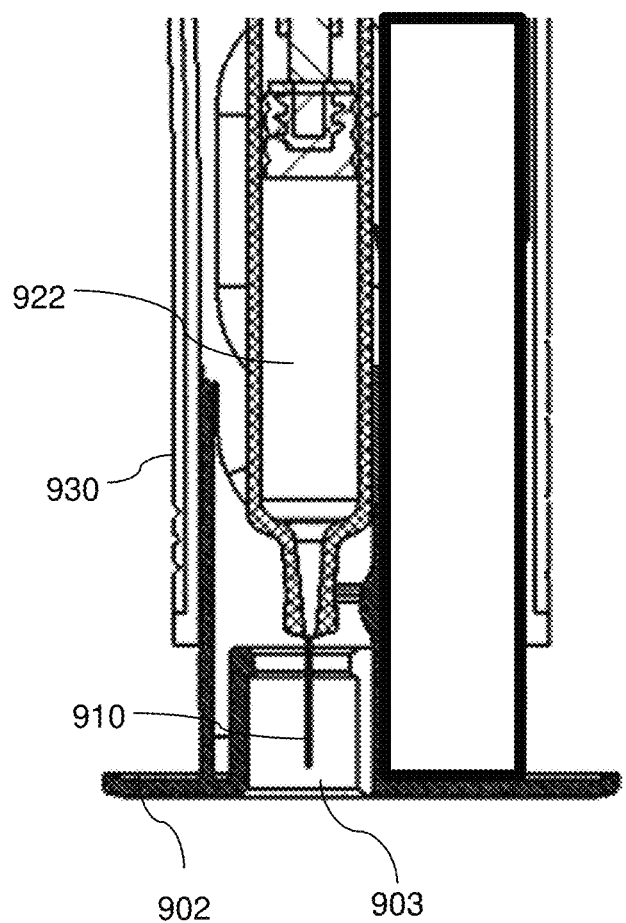
FIGS. 9A-9C are schematic diagrams an injector in accordance with an embodiment of the present invention.
Figure 9B:
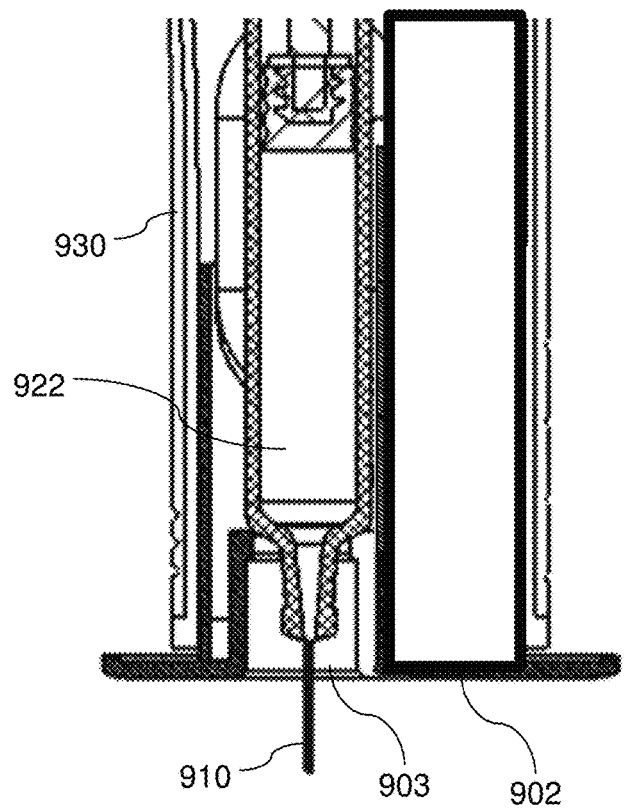
Figure 9C:
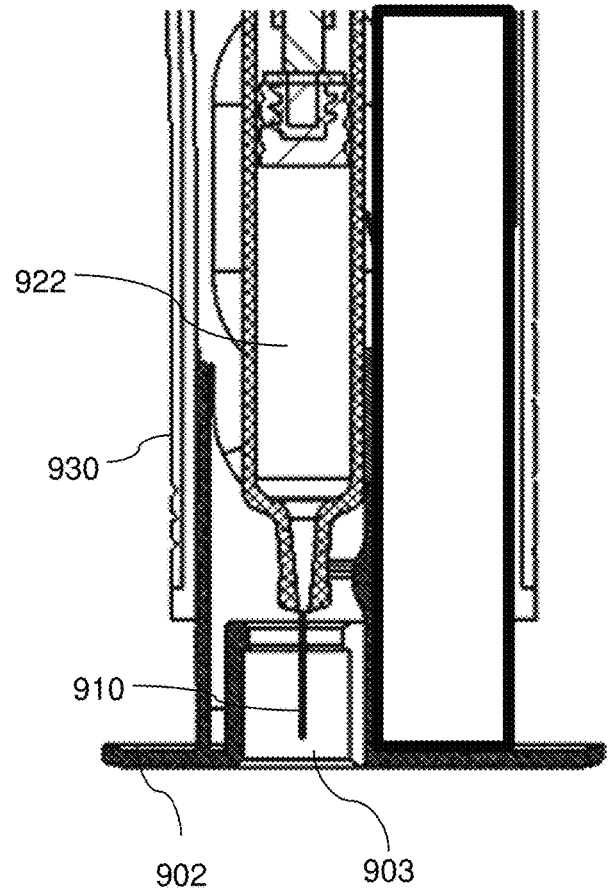

Stabilized Injector FIGS. 9A-9C are schematic cross sectional diagrams a stabilized pen injector in accordance with an embodiment of the present invention.

FIG. 9A illustrates a stabilized injector in a ready state in accordance with an embodiment of the current invention. Optionally, a standard syringe 922 with a straight needle 910 is mounted behind an adhesive base 902. Optionally, the injector is supplied with a sterile needle cap. For example, the needle cap may be removed through an opening 903 in base 902 before starting injection. To start injection a user optionally adheres base 902 to an injection site and/or pushes a housing 930 of the injector towards the injection site. For example, the pressure applied by the user may collapse base 902 towards housing 930 such that needle 910 protrudes through opening 903 into the injection site.

FIG. 9B illustrates a stabilized pen injector in an active state in accordance with an embodiment of the current invention.

In some embodiments, base 902 is retained in a collapsed state, for example, base 902 may be biased towards housing 930. Alternatively, a retaining and/or locking mechanism retains base 902 in the collapsed state. Optionally, an actuator delivers a drug through needle 910 into the subject while the adhesive retains the device on an injection site and/or while the device is retained in the active state.

In some embodiments, a user may pull housing 930 away from an injection site (for example at the end of drug delivery and/or before the end of drug delivery). For example, pulling housing 930 away from an injection site while base 902 remains adhered to the injection site overcomes a retaining mechanism and/or deploys a shield, for example by extending base 902 to a protecting state.

FIG. 9C illustrates a stabilized pen injector in a protected state in accordance with an embodiment of the current invention. For example, when base 902 is deployed from an active state to an extended state, it may permanently lock impeding access to needle 910 and/or preventing a needle stick injury.

In alternative embodiments, a stabilized pen injector optionally includes a needle insertion and/or retraction mechanism. For example, the insertion and/or retraction may perform insertion and/or retraction via an actuator and/or a stored energy source that is triggered for example by extending and/or collapsing base 910.

Alternative Patch Needle Mechanism

FIGS. 10A-10F are a schematic diagrams of a needle injection/retraction mechanism in accordance with an embodiment of the present invention. In some embodiments, a needle may be inserted and/or retracted by a linear movement mechanism. Optionally, the mechanism may be powered by a stored energy source, for example a coil spring.

Figure 10A:
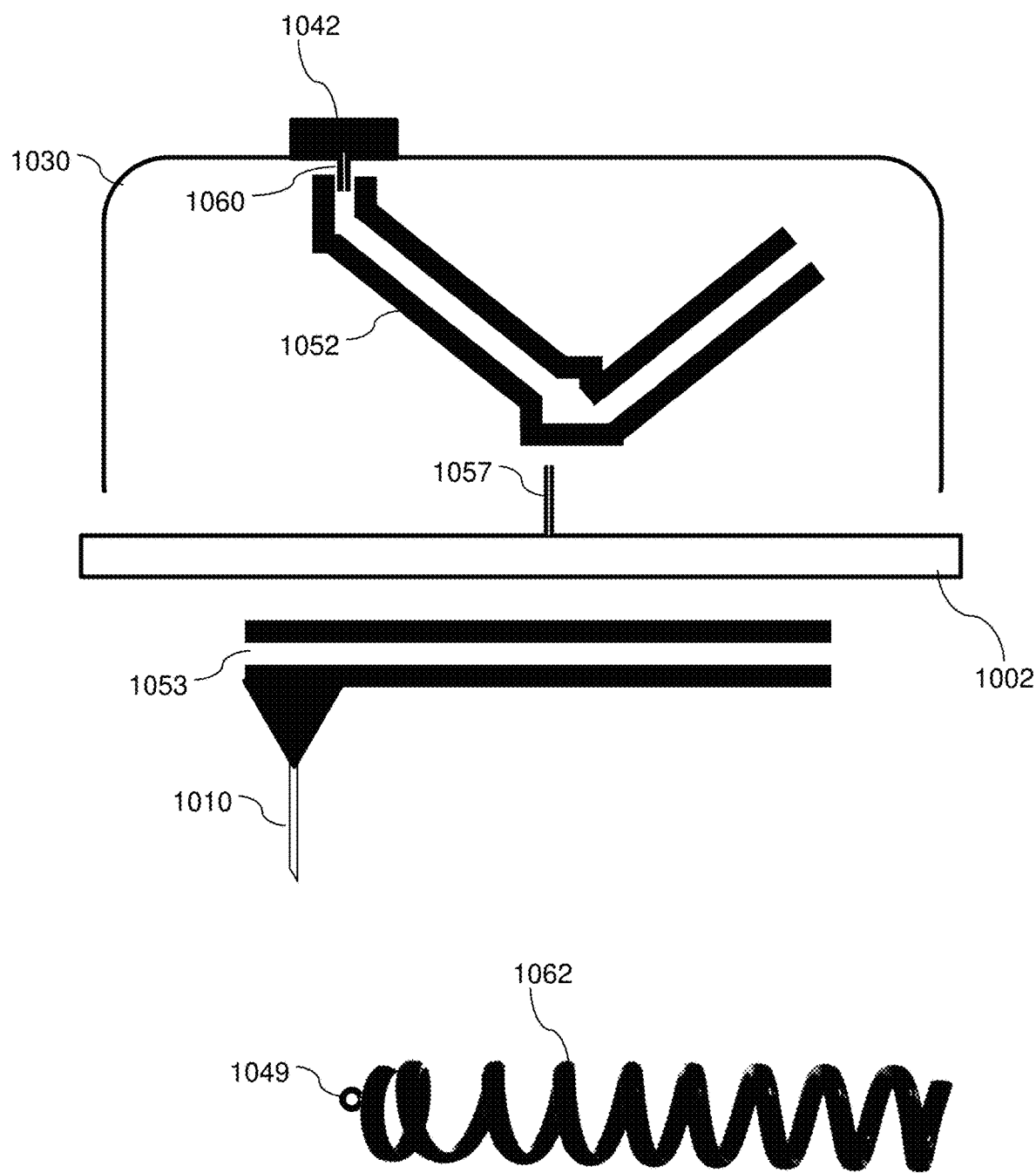
FIGS. 10A-10F are schematic diagrams of various states of injector in accordance with an embodiment of the present invention.

FIG. 10A is an exploded view of a needle injection/retraction mechanism in accordance with an embodiment of the present invention. In some embodiments, a mechanism may include an activation button 1042, a housing 1030, a base 1002 movably attached housing 1030, a fixed track 1052, a vertically movable track 1053 attached to a needle 1010, interference elements 1060 and 1057 (e.g. attached to button 1042 and base 1002 respectively), a pin 1049 attached to a coil spring 1062 stored energy source. For example, spring 1062 pulls pin 1049 rightward in the exemplary embodiment of FIGS. 10A-F.

Figure 10B:
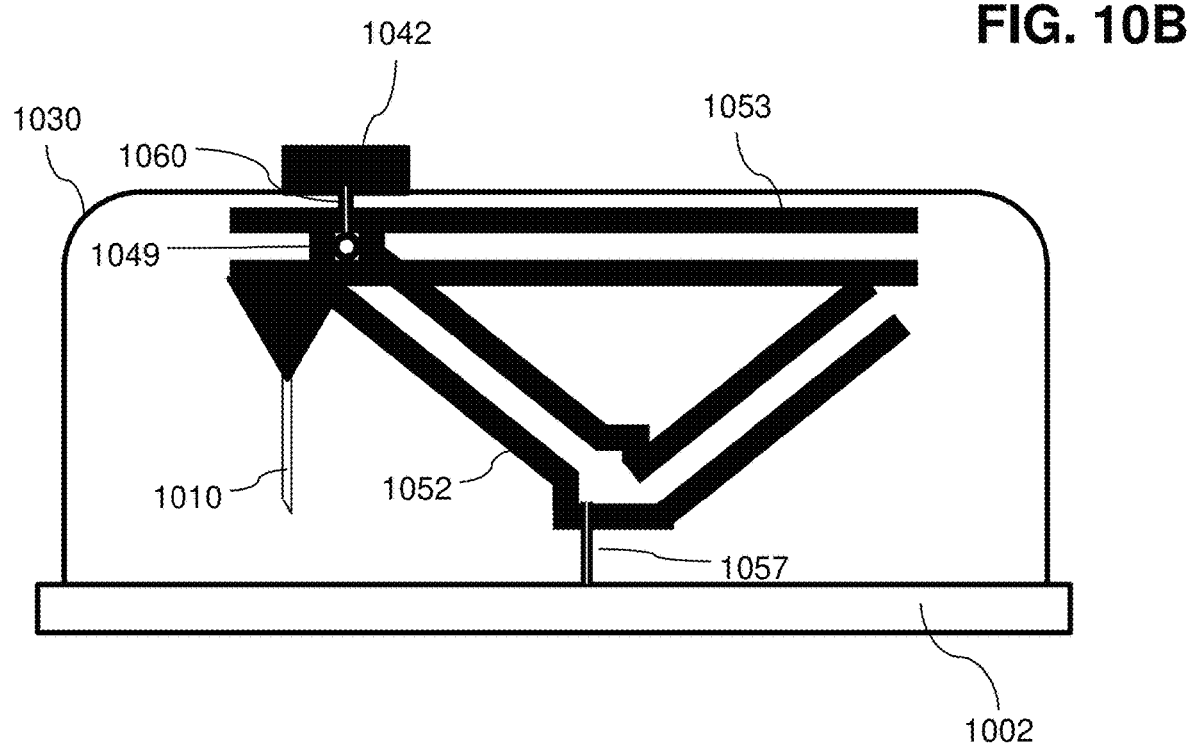

FIG. 10B illustrates a needle mechanism before placement on an injection site.

Optionally, before placement of the device, pin 1049 is prevented from moving to the right by a vertical portion of the wall of track 1052. Needle 1010 is optionally retracted upward and/or base 1002 is optionally extended downward.

Figure 10C:
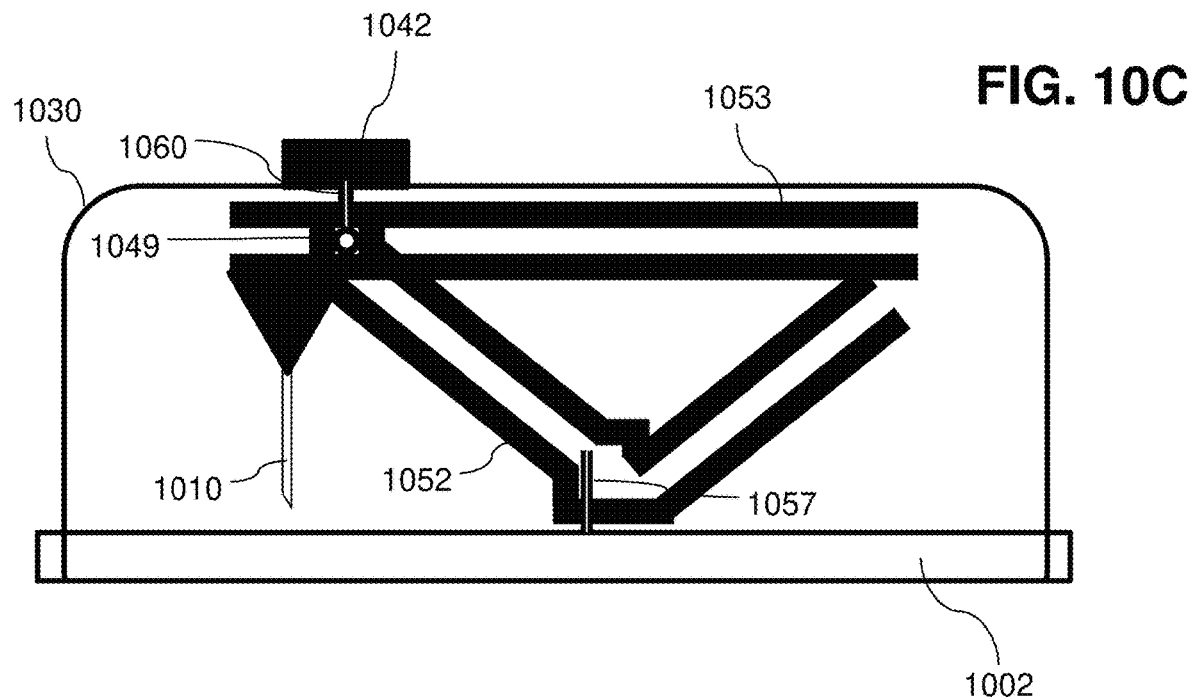

FIG. 10C illustrates a needle mechanism in a primed state after placement on an injection site in accordance with an embodiment of the present invention. Optionally, placement of the device on the injection site pushes up base 1002 and causes interference element 1057 to block the lower part of track 1052.

Figure 10D:
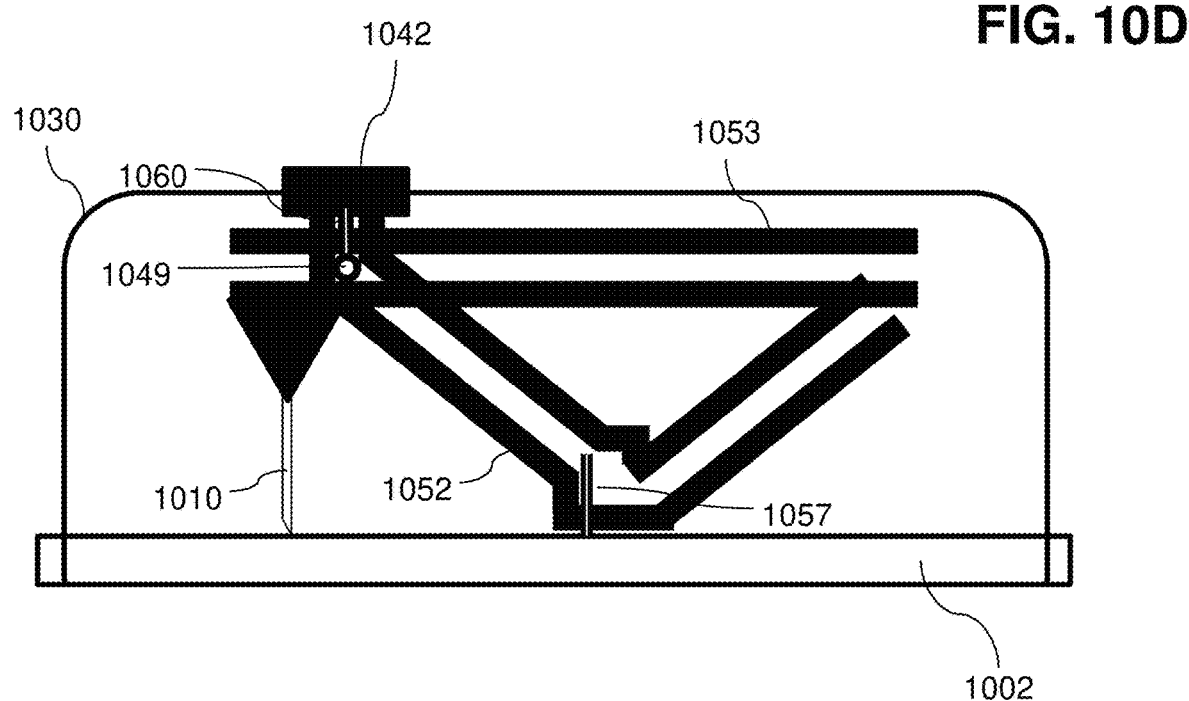

FIG. 10D illustrates a needle mechanism at the moment of depressing activation button 1042 in accordance with an embodiment of the present invention. Optionally, depressing button 1042 pushes interference element 1060 downward and/or pushes pin 1049 downward from the vertical part of track 1052 to a sloped portion of the track 1052. The rightward force of spring 1062 pulls pin 1049 against the sloping wall of track 1052.

Figure 10E:
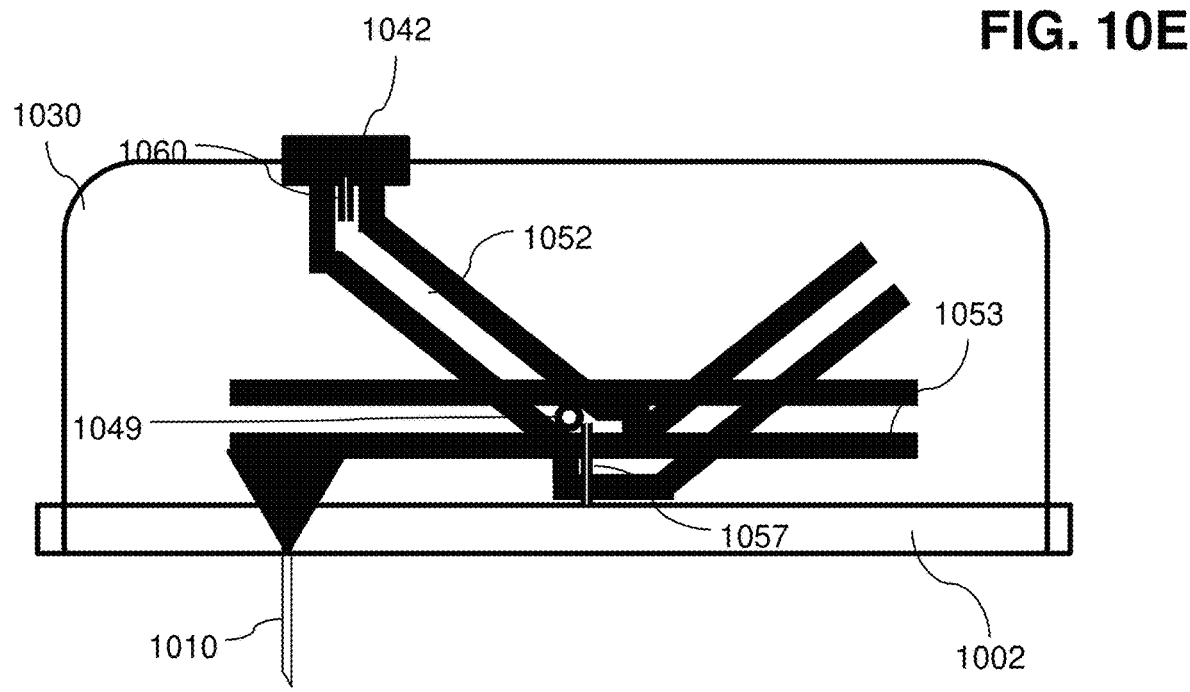

FIG. 10E illustrates a needle mechanism in an active state in accordance with an embodiment of the present invention. Pin 1049 is optionally pulled by rightward along track 1052. For example, as pin 1049 moves rightward, it moves downwards and/or pushes track 1053 downward and/or pushes needle 1010 out an opening in base 1002 into an extended position and/or into the injection site. Optionally, rightward motion of pin 1049 is stopped and/or needle 1010 is locked in the extended position when it contacts interference element 1057.

Figure 10F:
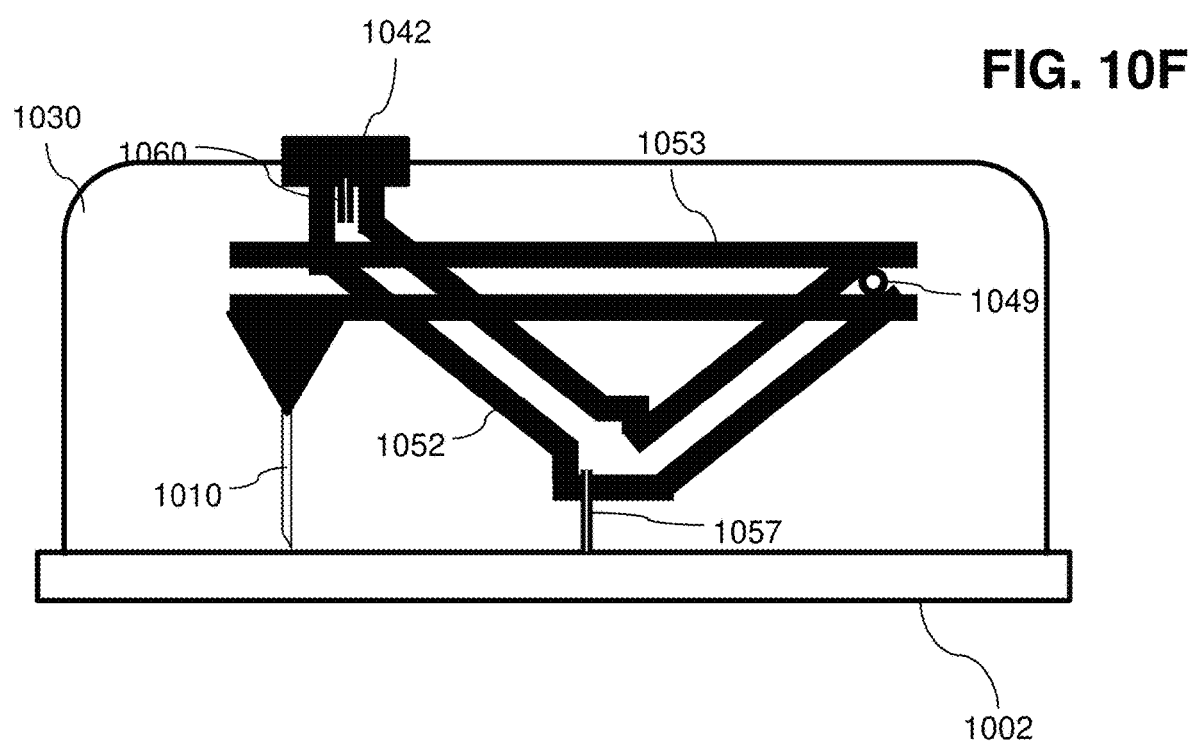

FIG. 10F illustrates a needle mechanism in a protected state in accordance with an embodiment of the present invention. Optionally the device is removed from the injection site by pulling housing 1030 away from the injection site. Base 1002, which is optionally adhered to the injection site, is optionally held to the injection site such that housing 1030 is pulled upwards with respect to base 1002. Optionally movement of housing 1030 with respect to base 1002 moves interference element 1057 out of track 1052. Once element 1057 has moved out of track 1052, pin 1049 is optionally freed to move rightward up track 1052. As pin 1049 moves rightward and upward, track 1053 and/or needle 1010 are pulled up into the retracted and/or protected position.

Exemplary Dimensions of a Drug Delivery Device

In some embodiments the payload of a reservoir (for example a syringe) may include, for example between 0.5 and 2 ml and/or between 2 and 7 ml and/or between 7 and 6 ml and/or between 7 and 10 ml of a drug and/or more. In some embodiments, the injector may discharge the entire payload as a single dose. A drug delivery device may include, for example, a patch injector, and/or an internally powered driver to drive the plunger and/or discharge the payload.

For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example, the driver may be designed to discharge the payload over a time period ranging between 20 and 120 seconds and/or between 120 and 600 seconds and/or between 600 seconds and an hour and/or between an hour and a day and/or longer.

In some embodiments, the apparatus may be preprogrammed to wait a fixed time delay ranging between 2 to 20 minutes and/or 20 minutes to an hour and/or an hour to 6 hours and/or 6 hours to 2 days after activation before beginning delivery of the substance. Optionally the length of the time delay may be an estimated time for a temperature sensitive component of the apparatus to reach a preferred working temperature. For example, the temperature sensitive component may include the drug and/or a battery.

In general, discharge may be driven by a driver. An internally powered driver may be powered by various mechanisms including for example a motor as discussed, including for example a DC motor, an actuator, a brushless motor, and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the present invention may include a reservoir part as discussed. For example, a reservoir may include a medicine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle, typically hollow, may optionally be connected to the syringe barrel. For example, the hollow of the needle may be in fluid communication with the interior of the barrel.

The needle may optionally be rigidly attached to the extension at the distal end of the barrel. The sterility of all and/or part of the needle may for example be protected by a protective cap. The protective cap may remain on the needle when the syringe is supplied and/or installed into an injector. For example, the medicine container may optionally include a cylindrical barrel rigidly attached to a needle. In some embodiments, a plunger may slide axially along the inside of the barrel to discharge a medicine payload. For example, the medicine may be discharged through the hollow needle. The protruding tip of the needle may be oriented at an angle to the axis of the barrel.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N and/or between 0.5 to 5 N. Optionally, the force required to inject the drug (for example the force on a syringe plunger) may range for example between 5 to 60 N. For example, the force required to inject the drug may depend on the injection rate and/or the viscosity of the drug and/or the syringe geometry and/or the needle dimensions.

In some embodiments, a needle protection mechanism may be triggered by a linear force greater than, for example, between 10 to 60 N.

For example, drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example, the mechanism may include a snap that gives way at 70 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguarding is triggered) may range for example between to 0.5 to 2 and/or from 2 to 7 and/or from 7 to 10N*cm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example, the driver may apply torque to threaded element pushing a plunger. When the torque on the driver reaches a threshold value, the needle may be released and/or retracted and/or a needle shield may be deployed. Alternatively or additionally, the trigger mechanism may require both a torque and a linear force. For example, requiring both a torque and a linear stress may prevent premature activation due to momentary friction.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 70 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate.

For example an expected time of discharge may range for example between 24 to 78 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 70 cp) and/or between 120 seconds and 3 minutes for larger volumes and/or viscosities. In some embodiments, injection times may be longer. The length of the injection time may be determined by considerations other than viscosity and/or volume.

In some embodiments, the reservoir may have a length ranging for example between 20 and 72 and/or 72 and 78 mm and/or 78 and 80 mm and/or 80 and 200 mm. In some embodiments an internal cylindrical space of a reservoir may have an average width ranging for example between 1 and 3 mm and/or 3 and 10 and/or 10 and 15 mm and/or 15 and 25 mm and/or 25 and 50 mm. Optionally a reservoir may have a circular cross section such that width is the diameter of the circle. In some embodiments, an extension may have a straight end portion with a length ranging for example between 1 and 3 mm or 3 and 7 mm or 7 and 8 or 8 and 10 mm or 10 and 15 mm or 15 and 50 mm. In some embodiments, the exposed straight portion of a needle may have a length ranging for example between 1 and 5 mm or 5 and 7 mm or 7 and 10 mm or 10 and 20 mm.

In some embodiments, an extension may have a sealing ring for a needle cap. The sealing ring may have a length ranging for example between 0.1 and 0.6 mm or 0.6 and 1 mm or 1 and 2.5 mm or 2.5 and 3 mm or 3 and 6 mm or 6 and 15 mm. In some embodiments a sealing ring may have an internal cavity with a length ranging for example between 0.5 and 1.5 mm/or 1.5 and 2.5 mm or 2.5 and 5 mm or 5 and 10 mm.

In some embodiments the sealing ring may have an external average width which may also be an average outer diameter ranging for example between 1 and 7 mm or 7 and 5 mm or 5 and 10 mm or 10 and 20 mm. In some embodiments the sealing ring may have an internal average width which also may be an average inner diameter ranging for example between 1 and 3 mm or 3 and 7 mm or 7 and 10 mm or 10 and 18 mm. In some embodiments, the extension may have a neck (not including the sealing ring) with an average width which may be an average diameter ranging for example between 1 and 3 mm or 3 and 7 mm or 7 and 8 mm or 8 and 16 mm. Optionally the neck may have a non-uniform cross section (for example an I beam and/or cross shaped cross section) and/or a tapered cross section.

For a non-uniform cross section, an average outer width may be defined as the width of the smallest oval that can enclose the neck averaged over the length of the neck. In some embodiments a fluid path between the extension and a reservoir cavity may include a 27 gauge needle or a needle ranging between 25 and 30 gauge or a needle ranging between 20 and 25 gauge or a needle ranging between 30 and 32 gauge. In some embodiments a needle protruding from an extension may include a 27 gauge needle or a needle ranging between 25 and 30 gauge or a needle ranging between 20 and 25 gauge or a needle ranging between 30 and 32 gauge.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 7, from 1 to 5, from 2 to 7, from 2 to 6, from 3 to 6 etc., as well as individual numbers within that range, for example, 1, 2, 3, 7, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An injection device comprising:
    a base including a skin contact surface comprising an adhesive configured to adhere to an injection site;
    an adhesive protector liner removably covering the adhesive;
    a cartridge extending along a cartridge axis that is substantially parallel to an axis of the skin contact surface, the cartridge storing a pharmaceutical substance;
    an activation button configured to initiate injection of the pharmaceutical substance;
    a needle extending along a needle axis that is angularly offset from the cartridge axis when the skin contact surface is adhered to the injection site, wherein the needle defines a needle tip configured to move between an exposed position on a first side of said skin contact surface, and a shielded position on an opposite side of said skin contact surface; and
    a spring centered around an axis that is angularly offset with respect to the needle axis, wherein the spring is configured to both 1) transition the needle tip from the shielded position to the exposed position, and 2) subsequently transition the needle tip from the exposed position to the shielded position.

2. The injection device of claim 1, further comprising:
    a plunger configured to slide axially along an inside surface of the cartridge; and
    a plunger driver comprising:
        a screw assembly;
        a motor; and
        a battery.

3. The injection device of claim 2, wherein the screw assembly is a telescoping assembly configured to axially extend along the cartridge axis.

4. The injection device of claim 1, wherein the base defines an opening, and the needle is configured to extend through the opening when the needle is in the exposed position.

5. The injection device of claim 1, wherein the activation button extends through a top surface of the injection device opposite the base.

6. The injection device of claim 5, wherein the top surface defines a window.

7. The injection device of claim 5, wherein the top surface of the injection device comprises an indicator configured to indicate a status of the injection device.

8. The injection device of claim 1, wherein the needle is connected to a linear track that provides for vertical movement of the needle between the exposed position and the shielded position.

9. The injection device of claim 1, further comprising:
    an interference element configured to selectively prevent the spring from transitioning the needle from the exposed position to the shielded position.

10. The injection device of claim 1, wherein the spring is configured to rotate to transition the needle tip from the shielded position to the exposed position.

11. The injection device of claim 10, wherein the spring is configured to rotate to transition the needle tip from the exposed position to the shielded position.

12. The injection device of claim 1, wherein the cartridge defines a reservoir having a capacity between 0.5 ml and 2.0 ml.

13. The injection device of claim 1, wherein the cartridge defines a reservoir having a capacity between 2.0 ml and 7.0 ml.

14. The injection device of claim 1, wherein the cartridge defines a reservoir having a capacity between 7.0 ml and 10.0 ml.

15. The injection device of claim 1, further comprising a needle cap covering the needle tip when the needle tip is in the shielded position.

16. The injection device of claim 1, wherein the skin contact surface has a surface area between 1 $cm^2$ and 5 $cm^2$.

17. The injection device of claim 1, wherein the skin contact surface has a surface area between 5 $cm^2$ and 15 $cm^2$.

18. The injection device of claim 1, wherein the skin contact surface has a surface area between 15 $cm^2$ and 80 $cm^2$.

19. The injection device of claim 1, further comprising a sensor or a switch configured to detect movement of the base relative to the injection device.

20. The injection device of claim 1, wherein the spring is a torsion spring.

* * * * *